(12) United States Patent
Kinoshita et al.

(10) Patent No.: US 9,596,996 B2
(45) Date of Patent: Mar. 21, 2017

(54) BLOOD PRESSURE MEASUREMENT DEVICE, CONTROL METHOD OF ELECTRONIC SPHYGMOMANOMETER AND CONTROL PROGRAM OF ELECTRONIC SPHYGMOMANOMETER

(75) Inventors: Hiroyuki Kinoshita, Kyoto (JP); Shingo Yamashita, Kyoto (JP); Yukiya Sawanoi, Nara (JP); Mika Eto, Takatsuki (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1247 days.

(21) Appl. No.: 13/476,396

(22) Filed: May 21, 2012

(65) Prior Publication Data

US 2012/0232412 A1  Sep. 13, 2012

Related U.S. Application Data

(63) Continuation of application No. PCT/JP2010/070354, filed on Nov. 16, 2010.

(30) Foreign Application Priority Data

Nov. 20, 2009  (JP) ................................. 2009-265206

(51) Int. Cl.
  *A61B 5/02*  (2006.01)
  *A61B 5/022*  (2006.01)
  *A61B 5/0225*  (2006.01)

(52) U.S. Cl.
  CPC ........ *A61B 5/02225* (2013.01); *A61B 5/0225* (2013.01)

(58) Field of Classification Search
  USPC ................... 600/480–490, 595, 485–515
  See application file for complete search history.

(56) References Cited

U.S. PATENT DOCUMENTS 5,156,158 A * 10/1992 Shirasaki ........... A61B 5/02208
                                                      600/490
6,322,517 B1 * 11/2001 Yamamoto ............. A61B 5/022
                                                      600/490

(Continued)

FOREIGN PATENT DOCUMENTS

JP          63-035230 A      2/1988
JP          4-250133 A       9/1992

(Continued)

OTHER PUBLICATIONS

Patent Abstracts of Japan, Publication No. 06-245911, publication date Sep. 6, 1994 (1 page).

(Continued)

*Primary Examiner* — Michael Kahelin
*Assistant Examiner* — Mitchell E Alter
(74) *Attorney, Agent, or Firm* — Osha Liang LLP

(57) ABSTRACT

A sphygmomanometer, in a deflation process after inflation to prescribed pressure adjusts a drive voltage of an exhaust valve such that a deflation speed of a fluid bag achieves a prescribed deflation speed during an adjustment period, which is a prescribed period after starting deflation. When the adjustment period ends or when the deflation speed of the fluid bag achieves the prescribed speed, control is subsequently performed to fix the drive voltage of the exhaust valve and deflate the fluid bag while holding a gap of the exhaust valve constant.

15 Claims, 27 Drawing Sheets

(56) References Cited

U.S. PATENT DOCUMENTS

| | | | |
|---|---|---|---|
| 6,602,200 B1* | 8/2003 | Kubo | A61B 5/0225 600/485 |
| 2001/0048087 A1* | 12/2001 | Zimmermann | F02D 41/20 251/129.05 |
| 2005/0085738 A1* | 4/2005 | Stahmann et al. | 600/529 |
| 2006/0200007 A1* | 9/2006 | Brockway et al. | 600/300 |
| 2008/0312544 A1* | 12/2008 | Mochizuki | A61B 5/022 600/492 |
| 2009/0312652 A1* | 12/2009 | Yamakoshi | A61B 5/02255 600/493 |
| 2011/0201898 A1* | 8/2011 | Benco et al. | 600/300 |

FOREIGN PATENT DOCUMENTS

| | | |
|---|---|---|
| JP | 5-329113 A | 12/1993 |
| JP | 6-245911 A | 9/1994 |
| JP | 2008-099819 A | 5/2008 |

OTHER PUBLICATIONS

Patent Abstracts of Japan, Publication No. 05-329113, publication date Dec. 14, 1993 (1 page).
Patent Abstracts of Japan, Publication No. 2008-099819, publication date May 1, 2008 (1 page).
Patent Abstracts of Japan, Publication No. 04-250133, publication date Sep. 7, 1992 (1 page).
International Search Report issued in PCT/JP2010/070354 mailed on Dec. 21, 2010, with English translation thereof (2 pages).

* cited by examiner

BLOOD PRESSURE MEASUREMENT DEVICE, CONTROL METHOD OF ELECTRONIC SPHYGMOMANOMETER AND CONTROL PROGRAM OF ELECTRONIC SPHYGMOMANOMETER

TECHNICAL FIELD

This invention relates to a blood pressure measurement device, a control method of an electronic sphygmomanometer and a control program of an electronic sphygmomanometer, and more particularly to a blood pressure measurement device for measuring blood pressure using an arm band (cuff) containing a fluid bag, a control method of an electronic sphygmomanometer and a control program of an electronic sphygmomanometer.

BACKGROUND ART

One method of calculating blood pressure employing an electronic sphygmomanometer is an oscillometric method for calculating blood pressure by deflating an arm band (cuff) containing a fluid bag that is wrapped around a part of a living body, and taking the change in volume of the fluid bag conveyed through the change in volume of the compressed blood vessels as a change in pressure (pressure pulse wave amplitude) of the fluid bag.

A characteristic of the fluid bag is that the pressure of the fluid bag and the volume of the fluid bag are related as shown in FIG. 24. That is, referring to FIG. 24, in the area shown in portion A where the pressure of the fluid bag is low, the volume of the fluid bag increases sharply relative to the increase in pressure of the fluid bag. Also, as the pressure of the fluid bag increases, the rate of increase of the volume of the fluid bag gradually decreases relative to the increase in pressure of the fluid bag, as shown in portion B. FIG. 25 and FIG. 26 are diagrams respectively representing a change in volume of the fluid bag (B), a change of fluid density in the fluid bag (C), and a change in pressure of the fluid bag (D) following a change in volume of the blood vessels (A) when the fluid density in the fluid bag is low and when the fluid density in the fluid bag is high. Also, FIG. 27 and FIG. 28 are diagrams respectively representing a change in volume of the fluid bag (B) and a change in pressure of the fluid bag (C) following a change in volume of the blood vessels (A) when the discharge speed of fluid from the fluid bag is fast, that is, when the discharge rate per unit time is large, and when the discharge speed of fluid from the fluid bag is slow, that is, when the discharge rate per unit time is small. The following features can be interpreted from FIG. 25 to FIG. 28 in relationship to the detection accuracy of changes in the volume of blood vessels:

(1) Fluid density in the fluid bag is higher, the higher the pressure of the fluid bag;
(2) Because the change of fluid density in the fluid bag following a change in volume of the blood vessels is smaller the larger the volume of the fluid bag, the detection accuracy of changes in the volume of blood vessels is low;
(3) Because the change of fluid density in the fluid bag following a change in volume of the fluid bag is larger the higher the pressure in the fluid bag, the detection accuracy of changes in the volume of blood vessels increases, in the case of the same change in volume of the fluid bag;
(4) Because the size of the change in volume of the fluid bag resulting from a change in volume of the blood vessels changes depending on the discharge rate of fluid in the fluid bag, the detection accuracy of changes in the volume of blood vessels differs, even for the same pressure of the fluid bag; and
(5) Because a change in volume of the fluid bag resulting from a change in volume of the blood vessels is smaller the greater the discharge rate of fluid in the fluid bag, the detection accuracy of changes in the volume of blood vessels decreases.

Thus, with an electronic sphygmomanometer using the oscillometric method, the detection accuracy of changes in the volume of blood vessels is dependent on the fluid density in the fluid bag and the discharge rate of fluid from the fluid bag.

As shown in FIG. 29A to FIG. 29C, with a sphygmomanometer that deflates the fluid bag at a constant speed, the amount of fluid discharged from the fluid bag is controlled with a valve, according to variables such as the pressure of the fluid bag and the circumference of the measurement site (FIG. 29B), in order to deflate the fluid bag at a constant speed (FIG. 29A). Thereby, as shown in FIG. 29C, the pressure pulse wave amplitude relative to a constant change in volume of the blood vessels is larger in the area where the pressure of the fluid bag is higher, and the pressure pulse wave amplitude relative to a constant change in volume of the blood vessels is smaller in the area where the pressure of the fluid bag is lower. Also, because the amount of change in volume of the blood vessels following a change in pressure of the fluid bag differs depending on the circumference of the measurement site, these factors cause errors in blood pressure measurement.

JP 6-245911A (Patent Document 1) discloses technology for adjusting the discharge rate of a valve according to the circumference of the measurement site, or technology for providing a fluid storage unit in communication with the fluid bag, and performs control while holding the volume sum of the fluid bag and the fluid storage unit constant according to the wrapped circumference of the fluid bag around at the measurement site. The deflation speed can thereby be held constant, even if the circumference of the measurement site differs.

Also, JP 5-329113A (Patent Document 2) discloses a method in which volume change characteristics of the fluid bag relative to the pressure of the fluid bag are provided in advance, a signal indicating a change in pressure of the fluid bag is reconverted to a change in volume, and a blood pressure value is measured using the change in volume.

Also, JP 4-250133A (Patent Document 3) discloses a method of closing a valve for discharging fluid in the fluid bag to prevent attenuation of the change in volume of the blood vessels following a change in volume of the fluid bag in a pulse wave arrival interval.

Patent Document 1: JP 6-245911A
Patent Document 2: JP 5-329113A
Patent Document 3: JP 4-250133A

SUMMARY OF INVENTION

However, although differences in deflation speed due to differences in the circumference of the measurement site can be eliminated with the method disclosed in Patent Document 1, the pressure pulse wave amplitude changes depending on the pressure of the fluid bag, as a result of the discharge rate of the valve changing in conjunction with the pressure of the fluid bag in order to hold the deflation speed constant. Thus, even if control is performed while holding the volume sum of the fluid bag and the fluid storage unit constant, only differences in volume due to the circumference of the measurement site are eliminated, and the size of the change in pressure of the fluid bag relative to the change in volume of the blood vessels changes depending on the pressure of the fluid bag. Therefore, errors arise in the blood pressure measurement.

Also, with the method disclosed in Patent Document 2, the pressure and volume change characteristics of the fluid bag need to be provided in advance. However, because these change characteristics change infinitely depending on factors such as how the fluid bag is wrapped, the thickness of the arm, and the flexibility of the human body, sufficient correction cannot be performed. The method disclosed in Patent Document 2 is also impracticable, given the need for a plurality of complicated corrections (flow rate detection, size detection of measurement site, wrapped state detection, consistency detection of human body, etc.), and the need for large-scale equipment.

Also, although a change in volume of the blood vessels can be precisely interpreted as a change in pressure of the fluid bag with the method disclosed in Patent Document 3, difficulties are encountered during deflation because the valve is closed whenever a pulse wave appears.

In other words, with the methods disclosed in these patent documents, the flow rate of fluid discharged from the fluid bag differs depending on the circumference of the measurement site and the pressure of the fluid bag, in the case where blood pressure is measured while deflating the fluid bag, because the pressure and volume of the fluid bag are not in a proportional relationship. The detection accuracy of pressure pulse wave amplitude relative to a change in volume of the blood vessels thereby differs depending on the circumference of the measurement site, the pressure of the fluid bag and the like. Accordingly, the accuracy of blood pressure measurement is compromised, because errors occur in the size of the pressure pulse wave amplitude depending on factors such as the blood pressure value and the circumference of the measurement site, even for the same change in volume of the blood vessels.

Therefore, one or more embodiments of the present invention provides a blood pressure measurement device, a control method of an electronic sphygmomanometer and a control program of an electronic sphygmomanometer that are able to approximate the pressure pulse wave amplitude relative to a constant change in volume of blood vessels to a constant value, and improve the accuracy of blood pressure measurement, by configuring the flow rate of fluid from the fluid bag and the deflation speed in a proportional relationship.

A blood pressure measurement device, in accordance with one or more embodiments of the present invention, includes a fluid bag, an inflation unit for injecting fluid into the fluid bag and inflating the fluid bag, a deflation unit including a valve provided in the fluid bag and for discharging fluid from the fluid bag and deflating the fluid bag, a sensor for measuring a change in internal pressure of the fluid bag, a blood pressure measurement unit for calculating a blood pressure value based on the change in internal pressure of the fluid bag obtained by the sensor in a deflation process of discharging fluid from the fluid bag by the deflation unit, and a control unit for controlling the inflation unit, the deflation unit and the blood pressure measurement unit. The control unit decides a gap of the valve which is a control amount for controlling a discharge rate of the fluid by the deflation unit such that the discharge rate is proportional to a deflation speed of the fluid bag in the deflation process, and controls the discharge rate by performing control so as to hold the gap of the valve at the decided gap in the deflation process, and the control unit corrects an influence of production tolerance of the valve, by adjusting the decided control amount such that the deflation speed of the fluid bag is within a prescribed range during a prescribed period from a start of the deflation process.

According to one or more embodiments of the present invention, the control unit further adjusts the adjusted control amount such that the deflation speed of the fluid bag is faster than a prescribed speed, during measurement performed after the prescribed period.

According to one or more embodiments of the present invention, the control unit further adjusts the adjusted control amount, when a pulse pressure superimposed on the internal pressure of the fluid bag is equal to or greater than a prescribed frequency is detected in the deflation process.

According to one or more embodiments of the present invention, the control unit adjusts a drive voltage for driving the valve as the control amount.

According to one or more embodiments of the present invention, the control unit adjusts a consumption current of the valve as the control amount.

According to one or more embodiments of the present invention, the control unit judges whether the deflation speed of the fluid bag is within the prescribed range by comparing a consumption current of the valve with a threshold.

According to one or more embodiments of the present invention, the prescribed period is a period from the start of the deflation process until at least one pulse beat prior to a pulse wave initially being superimposed on the internal pressure of the fluid bag in the deflation process.

According to one or more embodiments of the present invention, the control unit decides the gap of the valve which is the control amount so as to achieve a deflation speed at which at least a prescribed number of pulse beats is included in a time taken for the internal pressure of the fluid bag to change from a systolic blood pressure to a diastolic blood pressure.

A blood pressure measurement device, in accordance with one or more embodiments of the present invention, includes a fluid bag, an inflation unit for injecting fluid into a fluid bag and inflating the fluid bag, a deflation unit including a valve provided in the fluid bag and for discharging fluid from the fluid bag and deflating the fluid bag, a sensor for measuring a change in internal pressure of the fluid bag, a blood pressure measurement unit for calculating a blood pressure value based on the change in internal pressure of the fluid bag obtained by the sensor in a deflation process of discharging fluid from the fluid bag by the deflation unit, and a control unit for controlling the inflation unit, the deflation unit and the blood pressure measurement unit. The control unit decides a gap of the valve which is a control amount for controlling a discharge rate of the fluid by the deflation unit such that the discharge rate is proportional to a deflation speed of the fluid bag in the deflation process, and controls the discharge rate by performing control so as to hold the gap of the valve at the decided gap in the deflation process, and the control unit corrects an influence of an environmental condition such as temperature or humidity, by adjusting the decided control amount such that the deflation speed of the fluid bag is within a prescribed range during a prescribed period from a start of the deflation process.

According to one or more embodiments of the present invention, the blood pressure measurement device further includes an input unit for inputting the environmental condition.

A blood pressure measurement device, in accordance with one or more embodiments of the present invention, includes a fluid bag, an inflation unit for injecting fluid into a fluid bag and inflating the fluid bag, a deflation unit including a valve provided in the fluid bag and for discharging fluid from the fluid bag and deflating the fluid bag, a sensor for measuring a change in internal pressure of the fluid bag, a blood pressure measurement unit for calculating a blood pressure value based on the change in internal pressure of the fluid bag obtained by the sensor in a deflation process of discharging fluid from the fluid bag by the deflation unit, and a control unit for controlling the inflation unit, the deflation unit and the blood pressure measurement unit. The control unit decides a gap of the valve which is a control amount for controlling a discharge rate of the fluid by the deflation unit such that the discharge rate is proportional to a deflation speed of the fluid bag in the deflation process, and controls the discharge rate by performing control so as to hold the gap of the valve at the decided gap in the deflation process, and the control unit corrects an influence of an installation inclination of the valve, by adjusting the decided control amount such that the deflation speed of the fluid bag is within a prescribed range during a prescribed period from a start of the deflation process.

A control method of an electronic sphygmomanometer, in accordance with one or more embodiments of the present invention, is a control method of an electronic sphygmomanometer that includes a fluid bag and an arithmetic operation unit for calculating a blood pressure value based on a change in internal pressure of the fluid bag. The fluid bag is provided with a valve, and the control method includes the steps of inflating the fluid bag to a prescribed pressure, deciding a voltage for driving the valve after the inflation, holding a gap of the valve at a decided gap and deflating the fluid bag by driving the valve at the decided voltage, calculating a blood pressure value from the change in internal pressure of the fluid bag in the deflation process, and outputting the blood pressure value. The step of deciding the voltage for driving the valve comprises deciding the gap of the valve serving as a control amount for controlling a discharge rate of the fluid such that the discharge rate is proportional to a deflation speed of the fluid bag in the deflation process.

A control program of an electronic sphygmomanometer, in accordance with a one or more embodiments of the present invention, is a control program for causing an electronic sphygmomanometer that includes a fluid bag and an arithmetic operation unit for calculating a blood pressure value based on a change in internal pressure of the fluid bag to execute a blood pressure measurement operation. The fluid bag is provided with a valve, and the program causes the electronic sphygmomanometer to execute the steps of inflating the fluid bag to a prescribed pressure, deciding a voltage for driving the valve after the inflation, holding a gap of the valve at a decided gap and deflating the fluid bag by driving the valve at the decided voltage, calculating a blood pressure value from the change in internal pressure of the fluid bag in the deflation process, and outputting the blood pressure value. The step of deciding the voltage for driving the valve comprises deciding the gap of the valve serving as a control amount for controlling a discharge rate of the fluid such that the discharge rate is proportional to a deflation speed of the fluid bag in the deflation process.

Embodiments of the present invention enable the detection accuracy of changes in the volume of blood vessels to be approximated to a constant value in a blood pressure measurement device, regardless of the pressure of the fluid bag. Blood pressure measurement errors can thereby be reduced. Also, the rate of change in the detection accuracy of changes in the volume of blood vessels can be approximated to a constant value, even if the volume of the fluid bag differs depending on the circumference of the measurement site. Blood pressure measurement errors can thereby be reduced. The need to correct the volume of the fluid bag which differs depending on the circumference of the measurement site is also thereby eliminated.

DETAILED DESCRIPTION OF INVENTION

Embodiments of the present invention are described hereinafter with reference to the drawings. In the following description, the same reference signs are given to the same components and constituent elements. The names and functions of thereof are also the same.

First Embodiment

Figure 1:
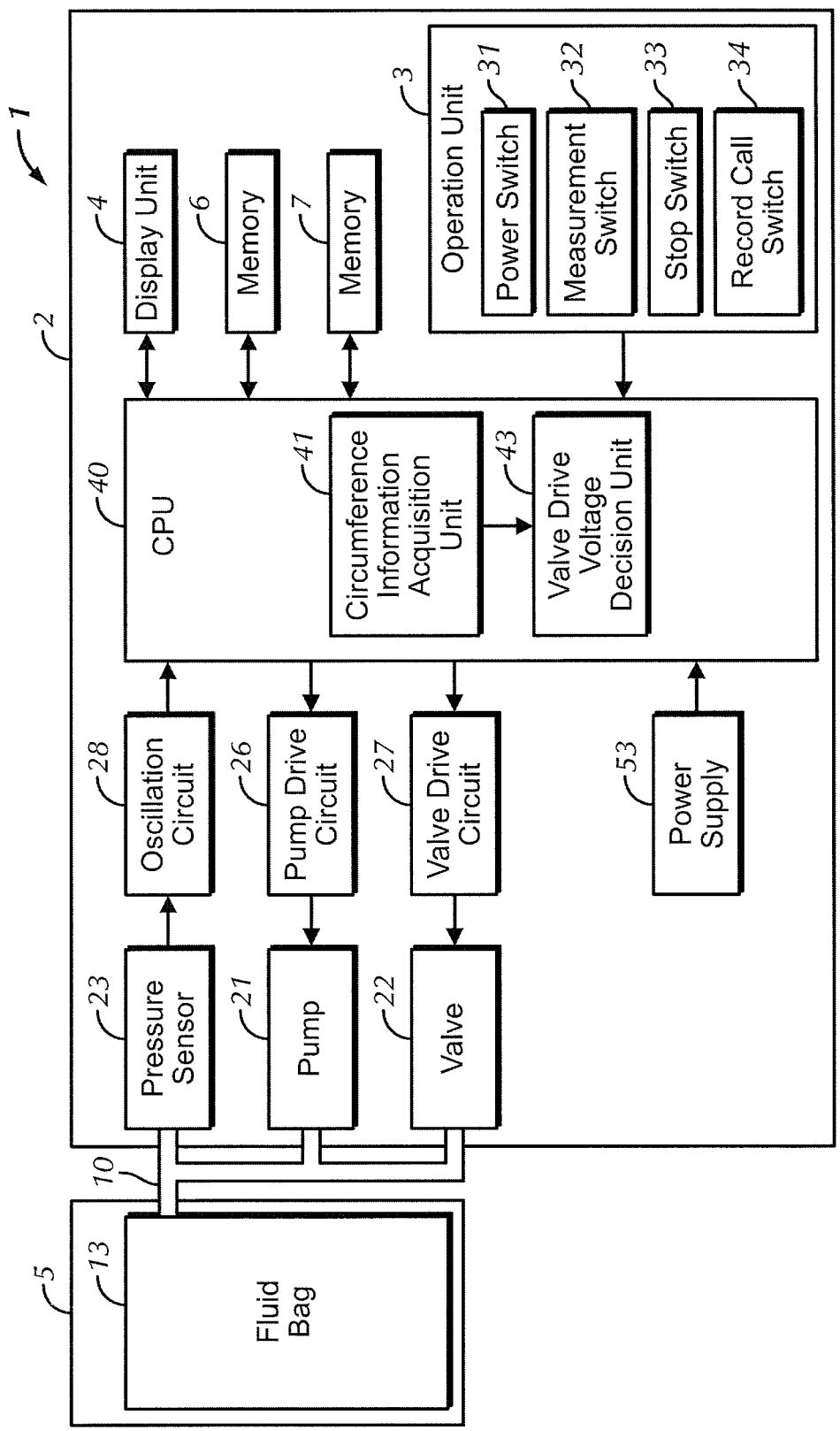
FIG. 1 is a block diagram showing a specific example of a hardware configuration of a sphygmomanometer serving as a blood pressure measurement device according to a first embodiment of the present invention.

Referring to FIG. 1, a sphygmomanometer 1 serving as a blood pressure measurement device according to a first embodiment of the present invention is provided with a main unit 2 and a cuff 5 that wraps around a measurement site, and these components are connected by a tube 10. An operation unit 3 constituted by switches and the like and a display unit 4 that displays measurement results and the like are arranged on the front of the main unit 2. The operation unit 3 includes a power switch 31 for instructing on/off of power supply, a measurement switch 32 for instructing that measurement be started, a stop switch 33 for instructing that measurement be stopped, and a record call switch 34 for calling and displaying measured values that are recorded. A fluid bag 13 is disposed in the cuff 5. Air, for example, is applicable as the fluid that is injected into the fluid bag 13 and discharged from the fluid bag 13. The fluid bag 13 is pushed against the measurement site by wrapping the cuff 5 around the measurement site. Measurement sites include the upper arm or the wrist, for example.

The fluid bag 13 is connected to a pressure sensor 23 for measuring change in internal pressure of the fluid bag 13, a pump 21 for injecting/discharging the fluid with respect to the fluid bag 13, and a valve 22. The pressure sensor 23, the pump 21 and the valve 22 are respectively connected to an oscillation circuit 28, a pump drive circuit 26 and a valve drive circuit 27, and, further, the oscillation circuit 28, the pump drive circuit 26 and the valve drive circuit 27 are all connected to a central processing unit (CPU) 40 that controls the entire sphygmomanometer 1.

The CPU 40, further, has connected thereto the display unit 4, the operation unit 3, a memory 6 serving as a work area when storing programs executed by the CPU 40 and executing the programs, a memory 7 that stores measurement results and the like, and a power supply 53.

The CPU 40 is driven when power is fed from the power supply 53. The CPU 40 includes a circumference information acquisition unit 41 and a valve drive voltage decision unit 43. These components are formed in the CPU 40 as a result of the CPU 40 executing a prescribed program stored in the memory 6 based on an operation signal input from the operation unit 3. The circumference information acquisition unit 41 acquires circumference information, which is the size of the measurement site, and inputs the acquired circumference information to the valve drive voltage decision unit 43. The valve drive voltage decision unit 43 decides the voltage (hereinafter, drive voltage E) for driving the valve 22 based on the circumference information. The CPU 40 outputs a control signal according to the drive voltage E decided by the valve drive voltage decision unit 43 to the valve drive circuit 27. Also, the CPU 40 executes a prescribed program stored in the memory 6 based on the operation signal input from the operation unit 3, and outputs a control signal to the pump drive circuit 26.

The pump drive circuit 26 and the valve drive circuit 27 drive the pump 21 and the valve 22 in accordance with the control signals. The pump 21 injects fluid into the fluid bag 13 when the drive thereof is controlled by the pump drive circuit 26 operating in accordance with the control signal from the CPU 40. The valve 22 discharges the fluid in the fluid bag 13 when the opening/closing and opening width (hereinafter, called a gap) thereof are controlled by the valve drive circuit 27 operating in accordance with the control signal from the CPU 40.

The pressure sensor 23 is a capacitance pressure sensor, and the capacitance value changes due to changes in the internal pressure of the fluid bag 13. The oscillation circuit 28 converts the change in the capacitance value of the pressure sensor 23 to an oscillation frequency signal, and inputs the oscillation frequency signal to the CPU 40. The CPU 40 executes prescribed processing based on the change in internal pressure of the fluid bag 13 obtained from the pressure sensor 23, and outputs the above control signals to the pump drive circuit 26 and the valve drive circuit 27 according to the processing result. Also, the CPU 40 calculates a blood pressure value based on the change in internal pressure of the fluid bag 13 obtained from the pressure sensor 23, performs processing for displaying the measurement result on the display unit 4, and outputs data and a control signal for causing display to the display unit 4. Also, the CPU 40 performs processing for storing the blood pressure value in the memory 7.

Figure 2:
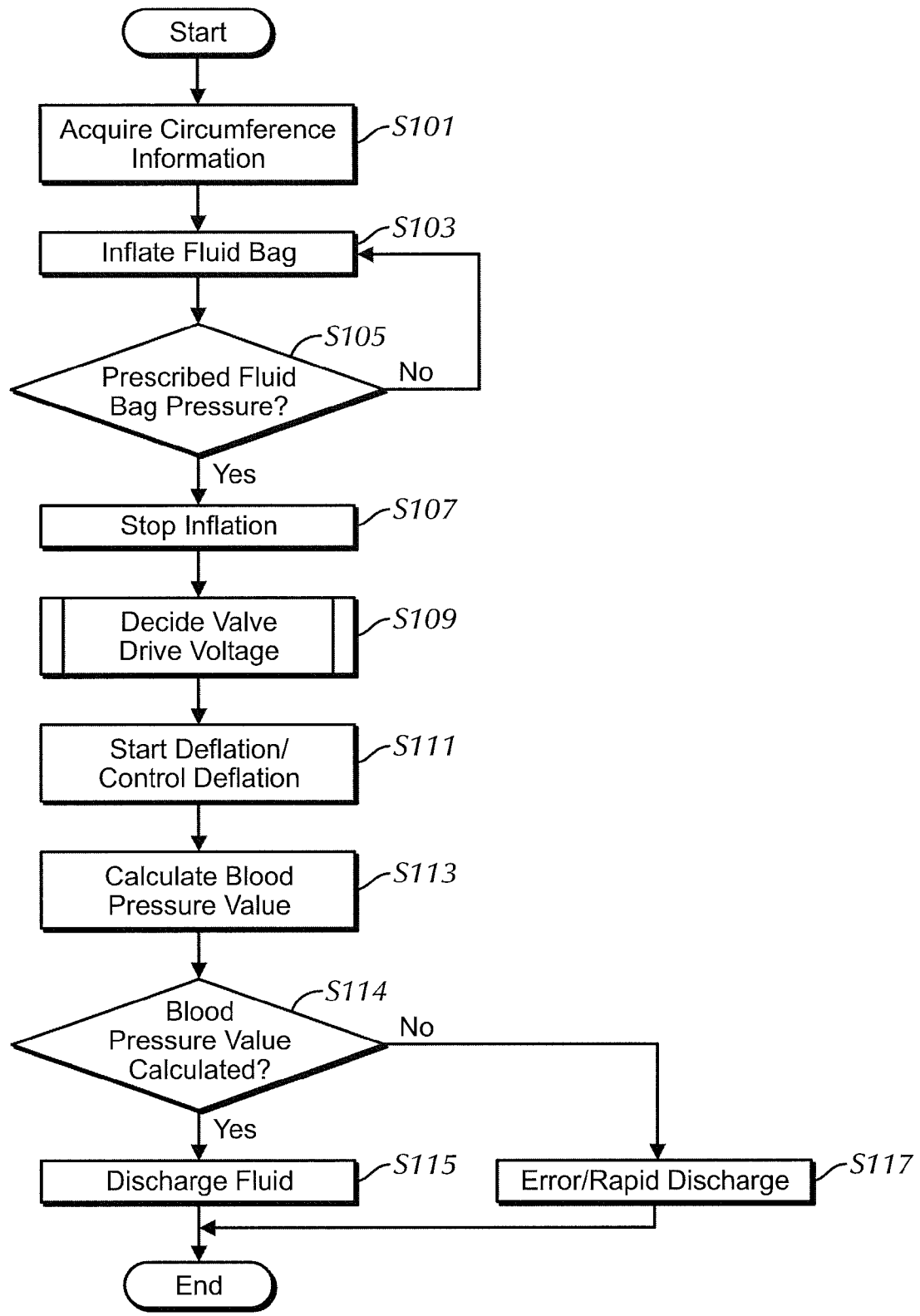
FIG. 2 is a flowchart showing a first specific example of processing executed at the timing at which a measurement switch is operated in the sphygmomanometer according to the first embodiment of the present invention.

FIG. 2 is a flowchart showing a first specific example of processing executed at the timing at which the measurement switch 32 is operated in the sphygmomanometer 1. The processing shown in the flowchart of FIG. 2 is realized as a result of the CPU 40 executing a prescribed program stored in the memory 6.

Referring to FIG. 2, the CPU 40 monitors input of operation signals from the operation unit 3, and on detecting that the measurement switch 32 was operated, the circumference information acquisition unit 41 of the CPU 40, at step S101, acquires circumference information representing the circumference of the measurement site, which is the size of the measurement site. Here, it is assumed that circumference information such as "thick" or "thin", for example, is input during measurement, using a switch or the liked constituting the operation unit 3, and that the circumference information acquisition unit 41 acquires circumference information from the operation signal of the operation unit 3.

Figure 3:
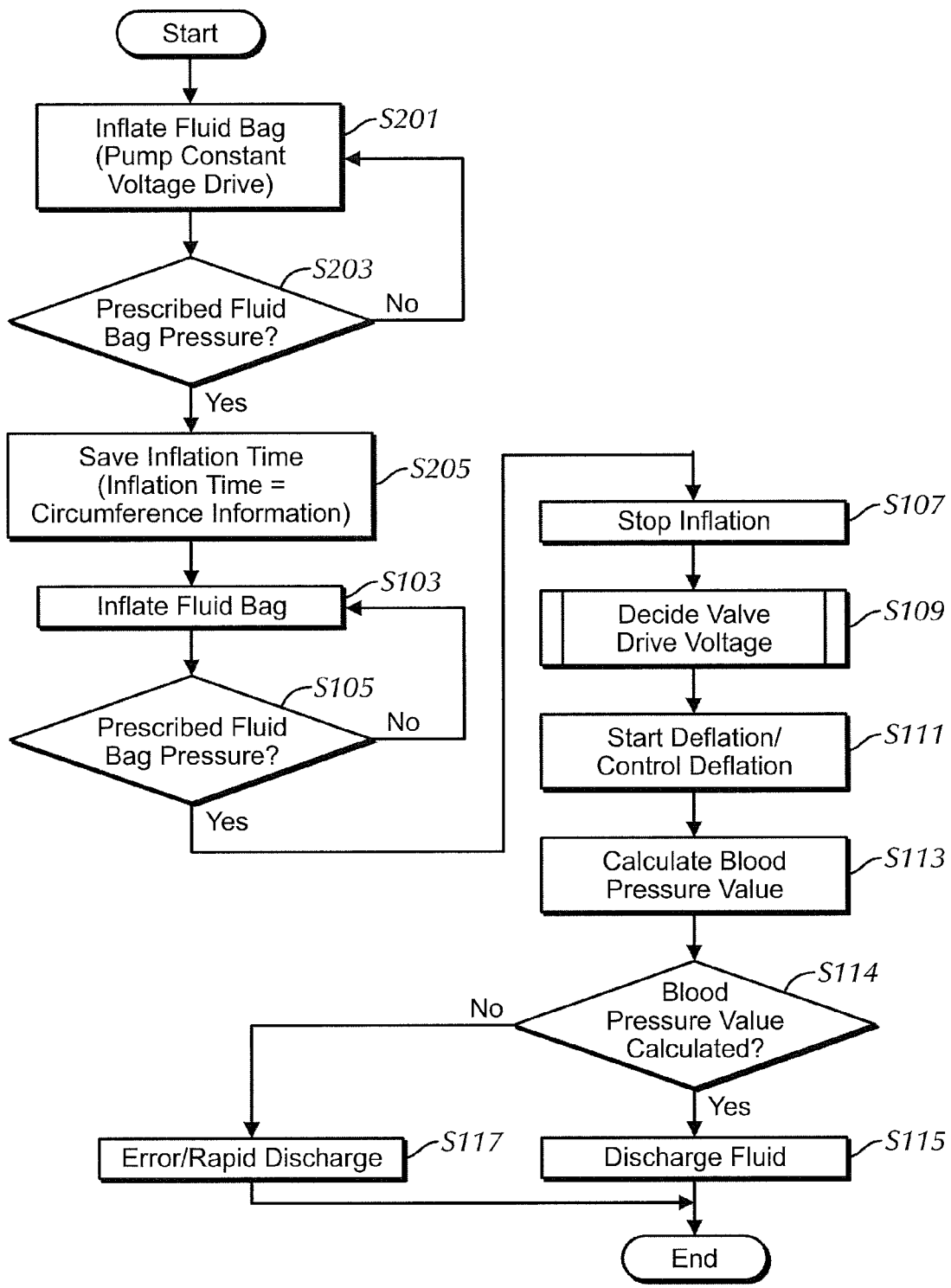
FIG. 3 is a flowchart showing a second specific example of processing executed at the timing at which the measurement switch is operated in the sphygmomanometer according to the first embodiment of the present invention.
Figure 4A:
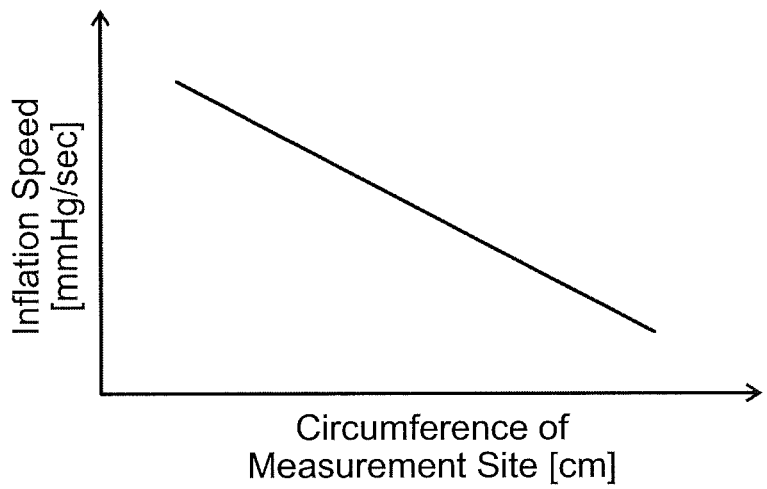
FIG. 4A is a diagram showing the relationship between the circumference of the measurement site and inflation speed.
Figure 4B:
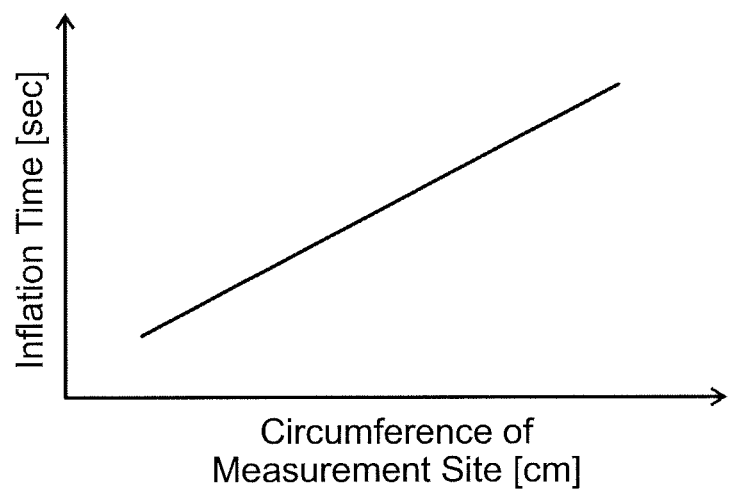
FIG. 4B is a diagram showing the relationship between the circumference of the measurement site and inflation time.

Note that the method of acquiring circumference information by the circumference information acquisition unit 41 is not limited to the above-mentioned method. For example, as a second specific example of processing executed at the timing at which the measurement switch 32 is operated in the sphygmomanometer 1, circumference information may be acquired at the processing of steps S201 to S205 instead of the above step S101, as shown in FIG. 3. Specifically, the CPU 40, at step S201, outputs a control signal for driving the pump 21 at a prescribed voltage defined in advance to the pump drive circuit 26, driving the pump 21 at the prescribed voltage and inflating the fluid bag 13 until the fluid bag 13 reaches a prescribed pressure defined in advance. When prescribed pressure is reached (YES at step S203), the CPU 40, at step S205, stores the inflation time taken for the fluid bag 13 to reach the prescribed pressure. As shown in FIG. 4A, inflation speed decreases the greater the circumference of the measurement site, in the case of the same drive voltage for driving the pump 21. Accordingly, the inflation time increases the greater the circumference of the measurement site, as shown in FIG. 4B. In other words, the inflation time taken for the fluid bag 13 to reach the prescribed pressure can be taken as an index representing the circumference of the measurement site. In view of this, the circumference information acquisition unit 41 acquires the inflation time stored at step S205 as circumference information. Note that circumference information can also be similarly obtained by the circumference information acquisition unit 41 from the number of rotations of the pump 21 and the pressure of the fluid bag 13, instead of the inflation time. Also, as another example, slide resistance is included in the fabric (not shown) serving as a mechanism for wrapping the fluid bag 13 around the measurement site, and the circumference information acquisition unit 41 may acquire circumference information from the resistance value obtained from the above slide resistance when the fluid bag 13 is wrapped around the measurement site.

At step S103 and S105, the CPU 40 outputs a control signal to the pump drive circuit 26, and inflates the fluid bag 13 until the fluid bag 13 reaches a prescribed pressure defined in advance. Once the prescribed pressure is reached (YES at step S105), the CPU 40, at step S107, outputs a control signal to the pump drive circuit 26, and stops inflation of the fluid bag 13. Thereafter, the valve drive voltage decision unit 43 of the CPU 40, at step S109, decides the drive voltage E of the valve 22 based on the circumference information acquired at step S101 or steps S201 to S205. At step S111, the CPU 40 outputs a control signal to the valve drive circuit 27 so as to drive the valve 22 while holding the drive voltage E decided at step S109, and starts deflation of the fluid bag 13. At step S113, the CPU 40 extracts the oscillation component accompanying the change in volume of the artery superimposed on the internal pressure of the fluid bag 13 obtained during deflation, and calculates a blood pressure value using a prescribed arithmetic operation. Note that when a blood pressure value is not calculated at the above step S113 because of the deflation speed at the above step S111 being too fast, or, conversely, when discharge does not progress because of the deflation speed at the above step S111 being too slow (NO at step S114), the CPU 40, at step S117, having judged that an error has occurred, outputs a control signal to the valve drive circuit 27 so as to release the valve 22 and rapidly discharges the fluid in the fluid bag 13. If this is not the case, that is, if a blood pressure value is calculated at the above step S113 (YES at step S114), the valve 22 is released in accordance with a control signal from the CPU 40 at step S115, and the fluid in the fluid bag 13 is discharged.

The processing to decide the drive voltage E by the valve drive voltage decision unit 43 in the above step S109 will be described.

Figure 5:
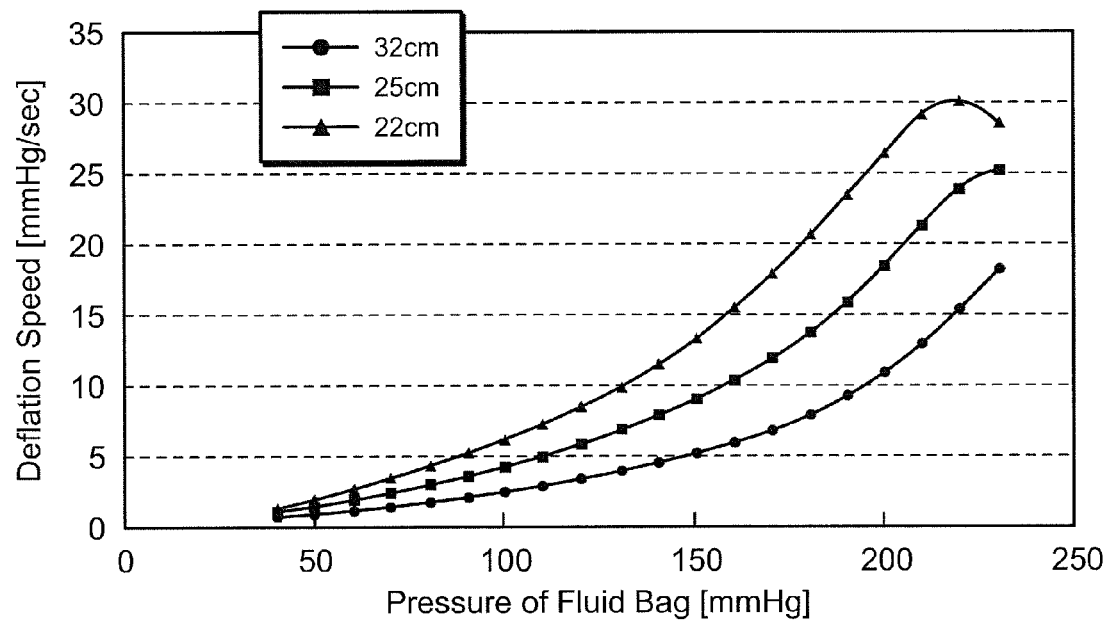
FIG. 5 is a diagram showing the degree of change in deflation speed relative to the pressure of the fluid bag in the case where the drive voltage of a valve is held constant for different circumferences of the measurement site.

Here, the degree of change in deflation speed relative to the pressure of the fluid bag in the case where the drive voltage E is held constant differs depending on the circumference of the measurement site, as shown in FIG. 5. Specifically, referring to FIG. 5, the degree of change in deflation speed is larger the smaller the circumference of the measurement site, and the degree of change in deflation speed is smaller the larger the circumference of the measurement site. In other words, the circumference of the measurement site can be viewed as a parameter for deciding the drive voltage E from the relationship shown in FIG. 5.

At the above step S109, the valve drive voltage decision unit 43 decides the drive voltage E utilizing the relationship shown in the above-mentioned FIG. 5. As a specific example, the valve drive voltage decision unit 43 decides the drive voltage E by substituting the circumference information acquired at the above step S101 or the above steps S201 to S205 into the following equation (1):

$$\text{Drive voltage } E = \alpha \times \text{circumference information} + \beta \quad (1).$$

Figure 6:
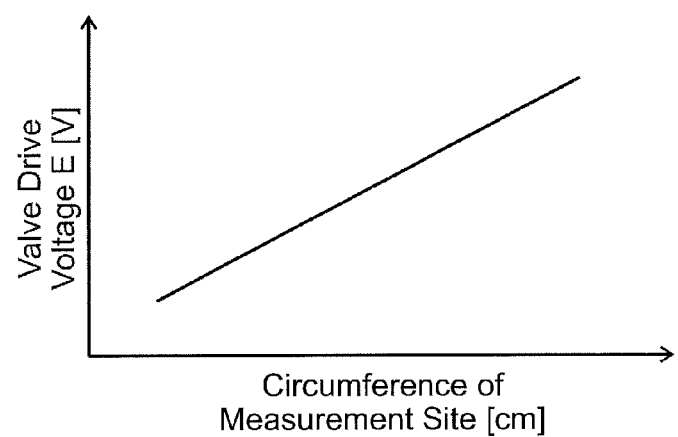
FIG. 6 is a diagram showing the relationship between the drive voltage of a valve and the circumference of the measurement site decided in the sphygmomanometer according to the first embodiment of the present invention.

By using the above-mentioned equation (1) at step S109, the drive voltage E is decided at a size proportional to the circumference of the measurement site, as shown in FIG. 6.

Figure 7:
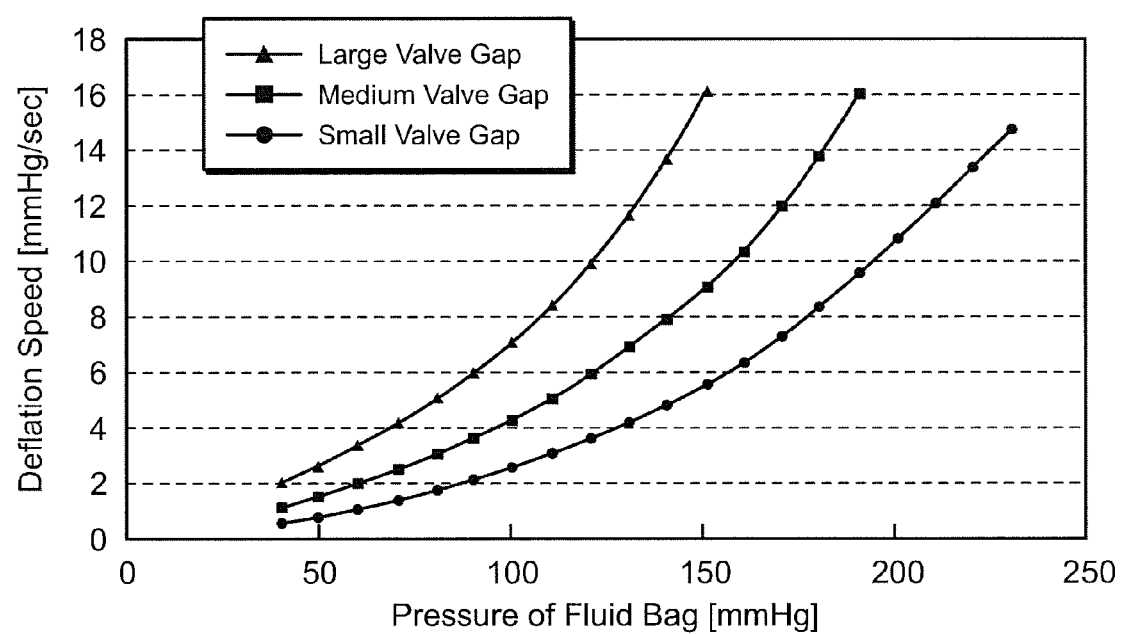
FIG. 7 is a diagram showing the degree of change in deflation speed relative to the pressure of the fluid bag in the case where the circumference of the measurement site is the same for different valve gaps.

Here, the degree of change in deflation speed relative to the pressure of the fluid bag 13 in the case where the circumference of the measurement site is the same differs depending on the size of the gap of the valve 22, that is, the size of the drive voltage, as shown in FIG. 7. Specifically, referring to FIG. 7, the degree of change in deflation speed increases the larger the gap of the valve 22, and the degree of change in deflation speed decreases the smaller the gap. According to one or more embodiments of the present invention, from the relationship shown in FIG. 7, the size of the gap is such that the deflation speed of the fluid bag 13 from calculation of systolic blood pressure to calculation of diastolic blood pressure is within a prescribed range of speeds. More specifically, according to one or more embodiments of the present invention, the size of the gap is such that the number of pulse beats detectable between the systolic blood pressure and the diastolic blood pressure during deflation is equal to or greater than a prescribed number. According to one or more embodiments of the present invention, the "prescribed number" is 5. This is because it is deemed appropriate that the size of the gap be set in consideration of the performance of the algorithm used to measure deflation so as control the deflation speed such that about five pulse beats are measured between the systolic blood pressure and the diastolic blood pressure during deflation, as also described in Japanese Patent No. 3179873 previously filed and disclosed by the applicant. Note that it is assumed that the size of a gap that allows five or more pulse beats to be measured between the systolic blood pressure and the diastolic blood pressure during deflation is obtained through experimentation or the like, and stored in advance in the memory 6. Specifically, according to one or more embodiments of the present invention, the value is about 5 mmHg/sec to 20 mmHg/sec. Accordingly, the coefficients $\alpha$ and $\beta$ in the above equation (1) can be set to values that result in the blood pressure deflation speed at which the pressure of the fluid bag 13 is in a range comparable with the blood pressure values being set within the target deflation speed range of about 5 mmHg/sec to 20 mmHg/sec. It is assumed that such coefficients $\alpha$ and $\beta$ are derived in advance through experimentation or the like, and stored in the memory 6 of the sphygmomanometer 1. Note that it is assumed in the above example that the drive voltage E is decided by inputting the acquired circumference information into the above equation (1) at step S109, although instead of the equation (1), the memory 6 may store a table defining the relationship between circumference information and drive voltages E, and the valve drive voltage decision unit 43 may read out the drive voltage E corresponding to the acquired circumference information from the table.

Variation

Figure 8:
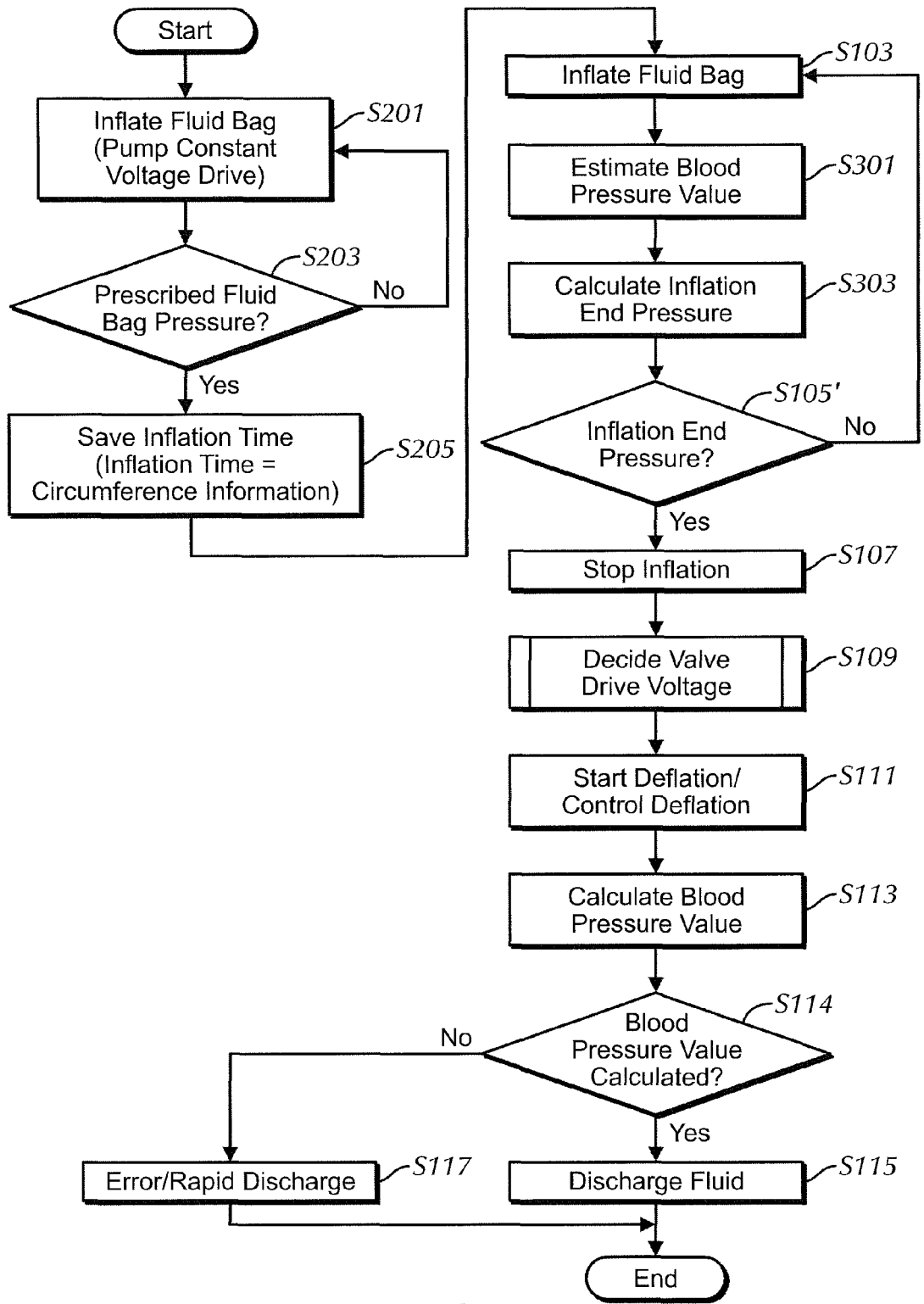
FIG. 8 is a flowchart showing a variation of the processing executed at the timing at which the measurement switch is operated in the sphygmomanometer according to the first embodiment of the present invention.

FIG. 8 is a flowchart showing a variation of the processing executed at the timing at which the measurement switch 32 is operated in the sphygmomanometer 1. In the processing shown in FIG. 8, the circumference of the measurement site is estimated based on the inflation time taken for the pressure of the fluid bag 13 to reach the prescribed pressure at steps S201 to S205. Similar to the second specific example shown in FIG. 3, and in the subsequent inflation process, the CPU 40, at step S301, estimates the systolic blood pressure value based on the change in internal pressure of the fluid bag 13 obtained from the pressure sensor 23, and, at step S303, calculates the pressure at the end of inflation of the fluid bag 13. The sphygmomanometer 1 is configured to calculate a blood pressure value based on the change in internal pressure of the fluid bag 13 obtained in the deflation process performed after inflating the fluid bag 13 to the prescribed pressure. Thus, at step S303, according to one or more embodiments of the present invention, the CPU 40 calculates a blood pressure value that is higher than the systolic blood pressure value estimated at step S301 by a prescribed pressure value as the inflation end pressure. Once the pressure of the fluid bag 13 reaches the inflation end pressure calculated at step S303 (YES at step S105'), subsequently the drive voltage E is decided similarly to the processing shown in FIG. 2 or FIG. 3, and a blood pressure value is calculated in the deflation process in which control is performed so as to drive the valve while holding the drive voltage E.

Note that in the variation, the valve drive voltage decision unit 43, at step S109, decides the drive voltage E in consideration of the systolic blood pressure value estimated at step S301, instead of or in addition to the above-mentioned relationship shown in FIG. 5. As a specific example, the valve drive voltage decision unit 43 decides the drive voltage E by substituting the circumference information acquired at the above step 101 or at the above steps S201 to S205 into the following equation (2):

$$\text{drive voltage } E = \alpha \times \text{circumference information} + \beta + \text{offset amount } S,$$

$$\text{offset amount } S = \text{estimated systolic blood pressure value} \times \gamma \quad (2).$$

Figure 9:
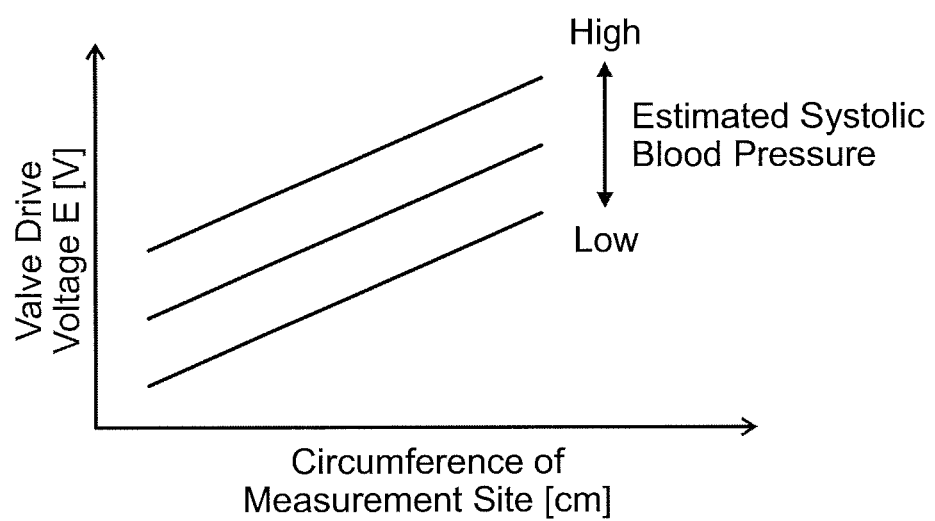
FIG. 9 is a diagram showing the relationship between the drive voltage of a valve and the circumference of the measurement site decided in the sphygmomanometer according to the variation of the first embodiment of the present invention.

By using the above-mentioned equation (2) at step S109 in the variation, the drive voltage E is decided at a size proportional to the circumference of the measurement site and at a size according to the estimated systolic blood pressure, as shown in FIG. 9.

From the relationship described using FIG. 7, according to one or more embodiments of the present invention, the size of the gap is such that the blood pressure deflation speed at which the pressure of the fluid bag 13 is in a range comparable with the blood pressure values is set within the target deflation speed range. Accordingly, the coefficient $\gamma$ in the above equation (2) can also be set to a value that results in the deflation speed from calculation of the systolic blood pressure to calculation of the diastolic blood pressure of the fluid bag 13 being set within the target deflation speed range of about 5 mmHg/sec to 20 mmHg/sec.

Figure 10A:
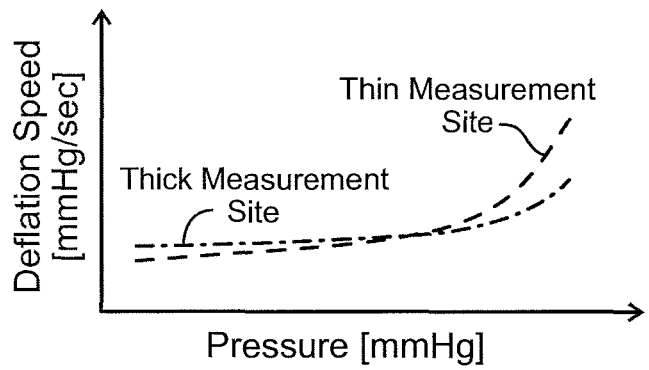
FIG. 10A is a diagram showing the relationship between the pressure of the fluid bag and deflation speed in the sphygmomanometer according to the first embodiment of the present invention.
Figure 10B:
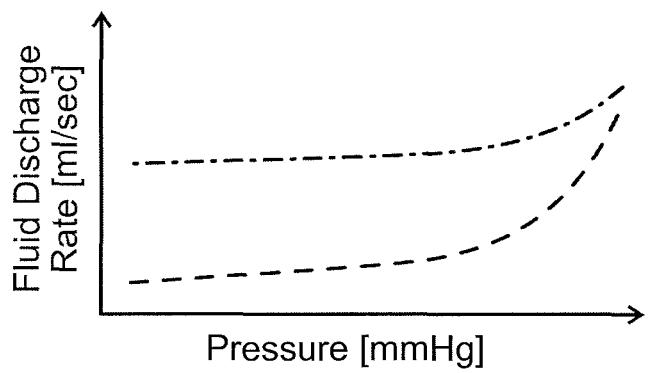
FIG. 10B is a diagram showing the relationship between the pressure of the fluid bag and the discharge rate of fluid in the sphygmomanometer according to the first embodiment of the present invention.

At the above step S111, control is performed by the CPU 40 to drive the valve 22 while holding the drive voltage E decided at the above step S109. That is, control is performed so that the gap of the valve 22 is constant during deflation. The deflation speed of the fluid bag 13 thereby changes as shown in FIG. 10A during deflation following the change in pressure of the fluid bag 13. That is, it is clear from FIG. 10A that in the case where the pressure of the fluid bag 13 falls below a given pressure, the deflation speed of the fluid bag 13 remains substantially unchanged by the subsequent change (decrease) in pressure, at substantially the same value, regardless of the size of the circumference of the measurement site. Also, the discharge rate from the valve 22 relative to the pressure of the fluid bag 13 changes as shown in FIG. 10B during deflation following the change in pressure of the fluid bag 13. That is, it is clear from FIG. 10B that in the case where the pressure of the fluid bag 13 falls below a given pressure, the discharge rate from the valve 22 remains substantially unchanged by the subsequent change (decrease) in pressure, at a value according to the circumference of the measurement site. In other words, it is clear from the relationships shown in FIG. 10A and FIG. 10B that performing control so that the drive voltage E is constant, that is, performing control to hold the gap of the valve 22 constant can be viewed as controlling the drive voltage E such that the discharge rate from the valve 22 and the deflation speed of the fluid bag 13 are in a proportional relationship.

Figure 10C:
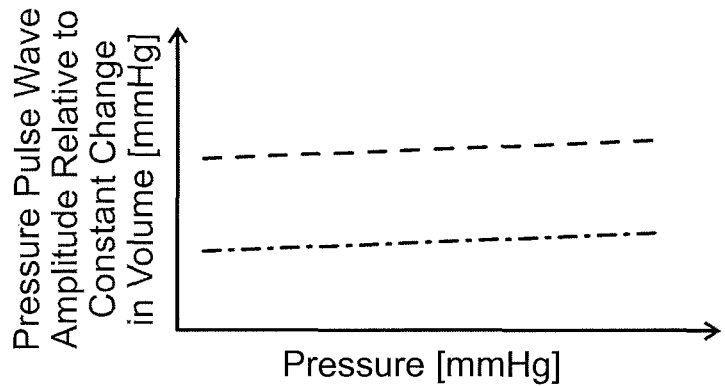
FIG. 10C is a diagram showing the relationship between the pressure of the fluid bag and the pressure pulse wave amplitude value relative to a constant change in volume in the sphygmomanometer according to the first embodiment of the present invention.

The CPU 40 performing control in this way enables the deflation speed and the flow rate of fluid from the fluid bag 13 to approximate a proportional relationship in the sphygmomanometer 1. The detection accuracy of changes in the volume of blood vessels can thereby be approximated to a constant value, and measurement accuracy can be improved. In other words, as shown in FIG. 10C, the pressure pulse wave amplitude relative to a constant change in volume can be held constant at a value according to the circumference of the measurement site, regardless of the change in pressure of the fluid bag 13.

Figure 11:
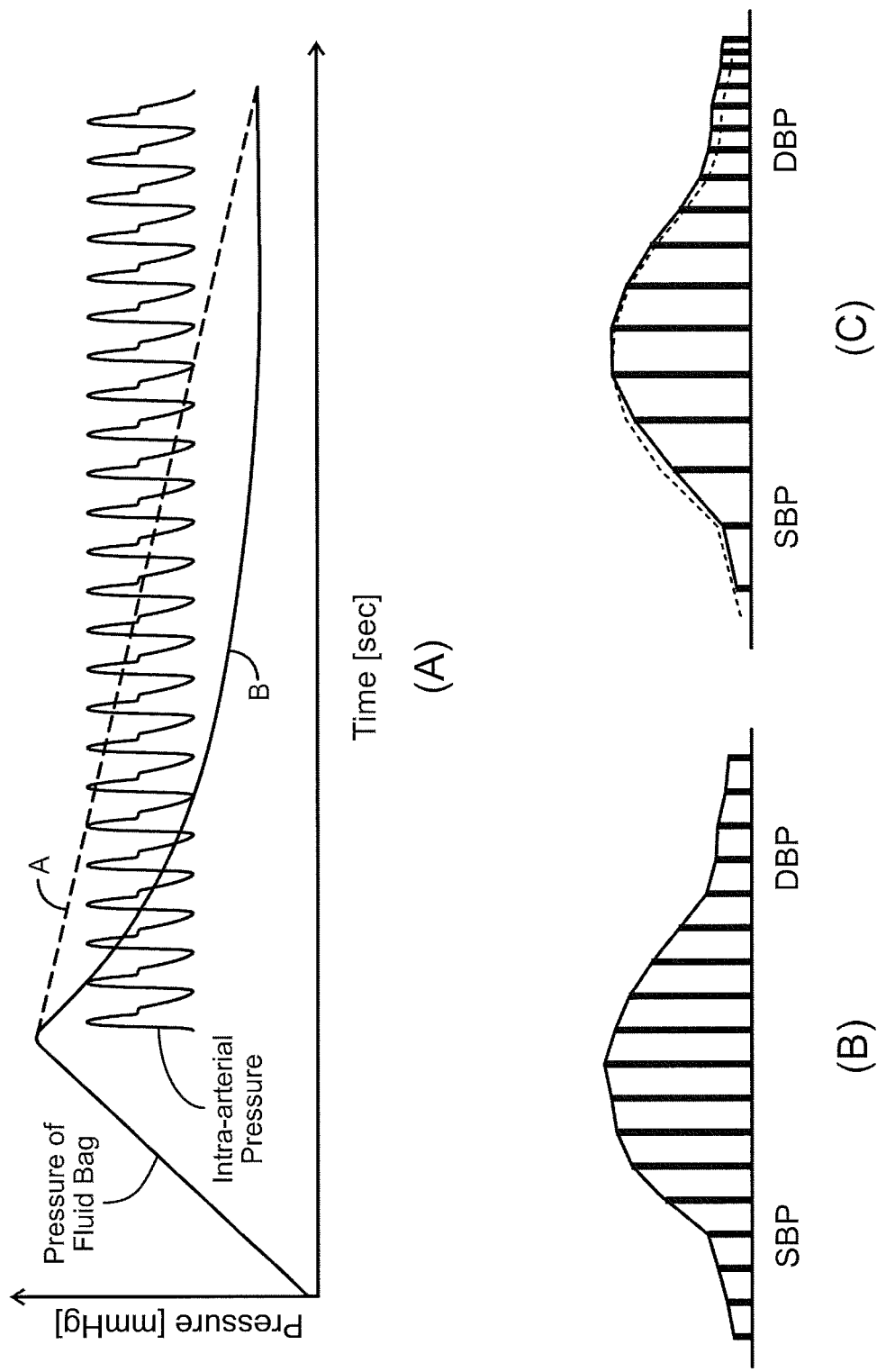
FIG. 11 is a diagram for illustrating the relationship between the pressure of the fluid bag and detected pulse wave amplitude.
Figure 25:
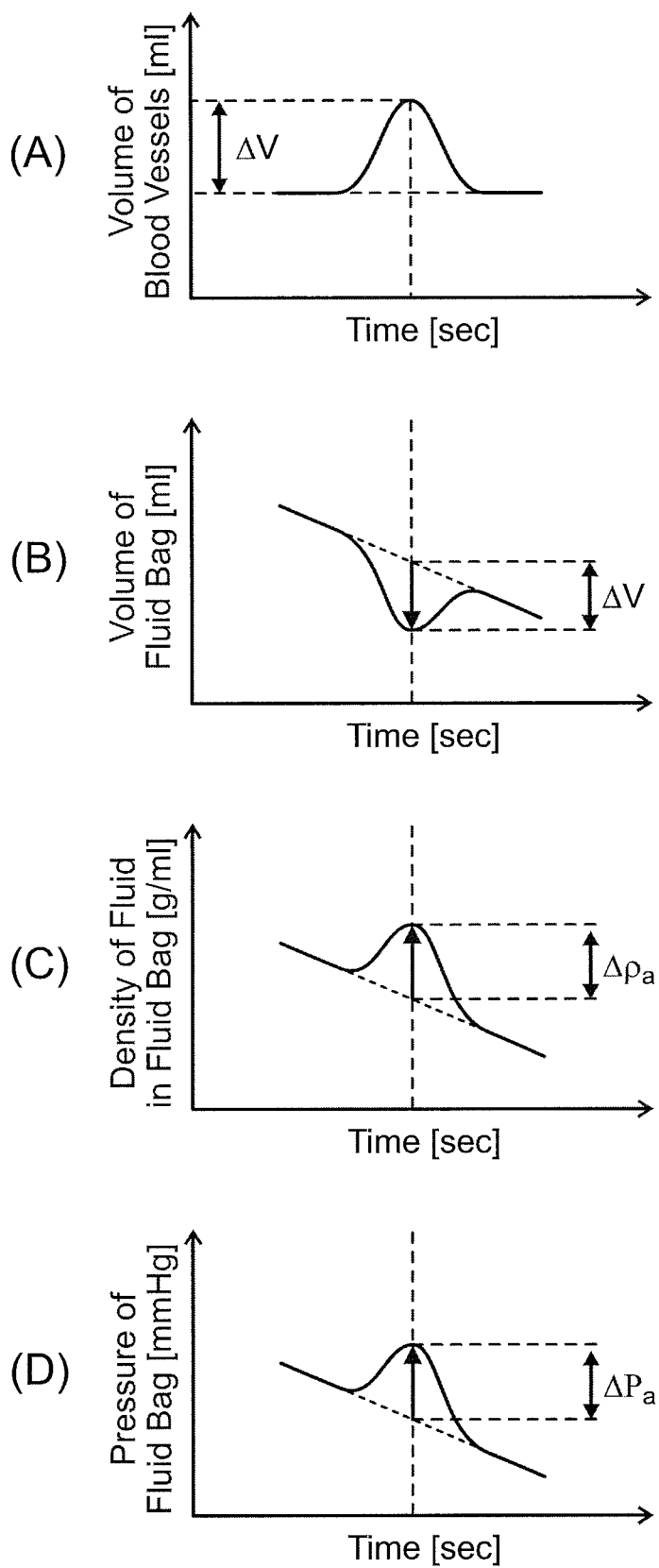
FIG. 25 is a diagram representing a change in volume of the fluid bag, a change of fluid density in the fluid bag, and a change in pressure of the fluid bag following a change in volume of the blood vessels when the fluid density in the fluid bag is low.
Figure 26:
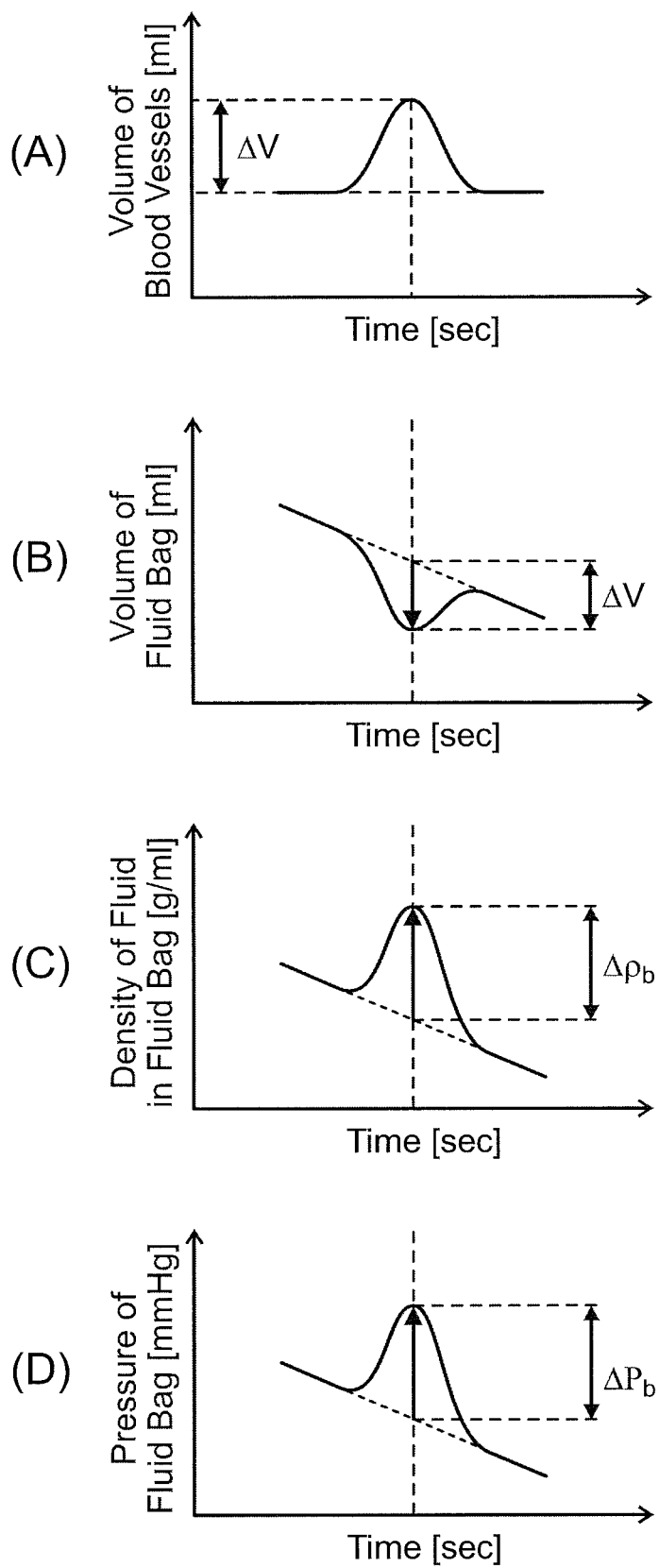
FIG. 26 is a diagram representing a change in volume of the fluid bag, a change of fluid density in the fluid bag, and a change in pressure of the fluid bag following a change in volume of the blood vessels when the fluid density in the fluid bag is high.
Figure 27:
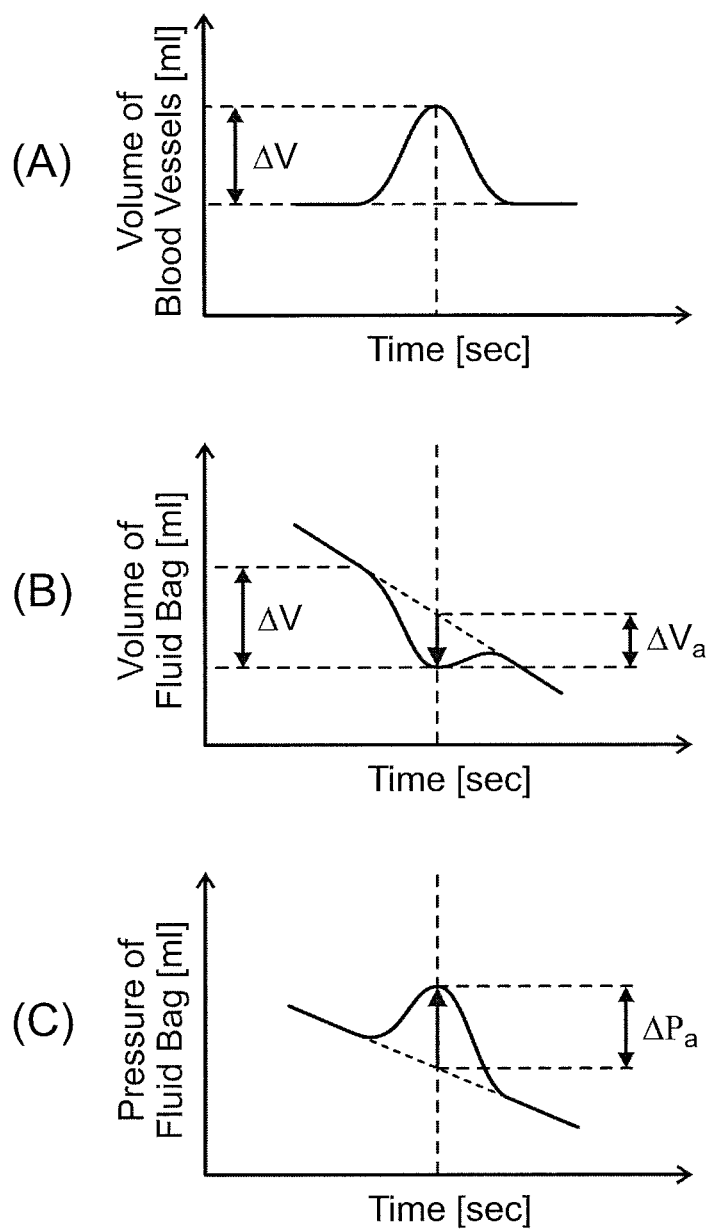
FIG. 27 is a diagram representing a change in volume of the fluid bag and a change in pressure of the fluid bag following a change in volume of the blood vessels, when the discharge speed of fluid from the fluid bag is fast, that is, when the discharge rate per unit time is high.
Figure 28:
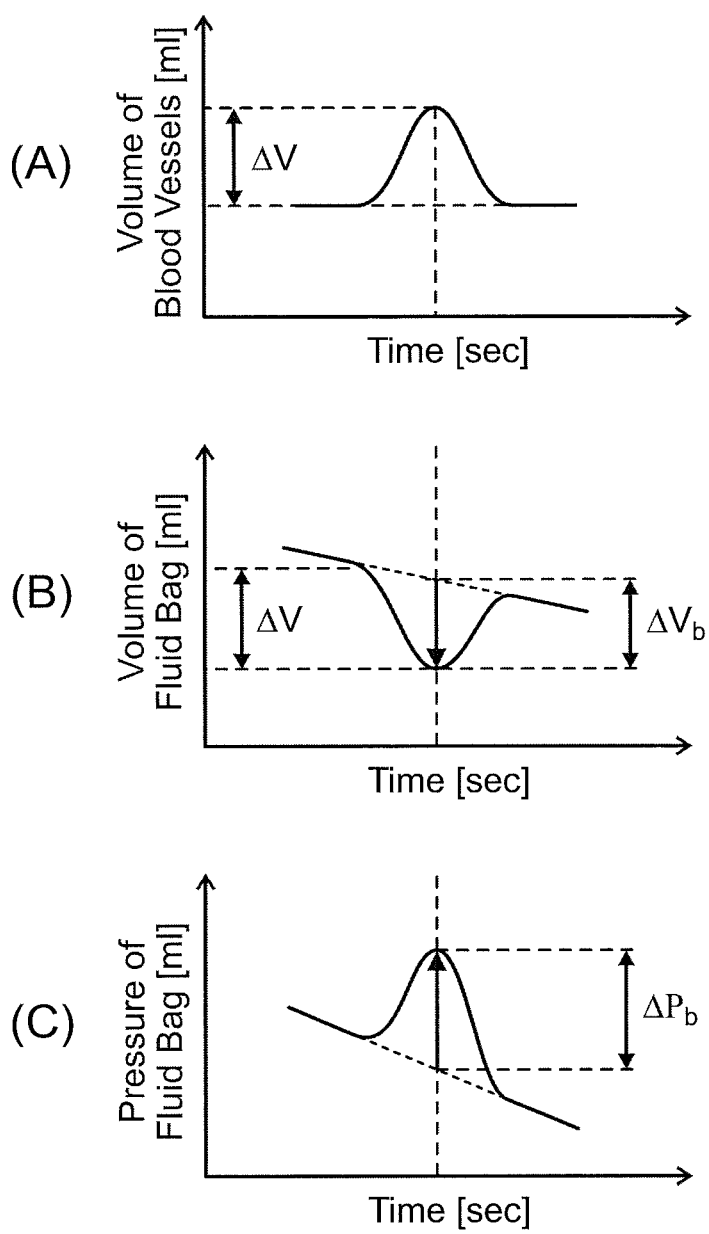
FIG. 28 is a diagram representing a change in volume of the fluid bag and a change in pressure of the fluid bag following a change in volume of the blood vessels, when the discharge speed of fluid from the fluid bag is slow, that is, when the discharge rate per unit time is low.
Figure 29A:
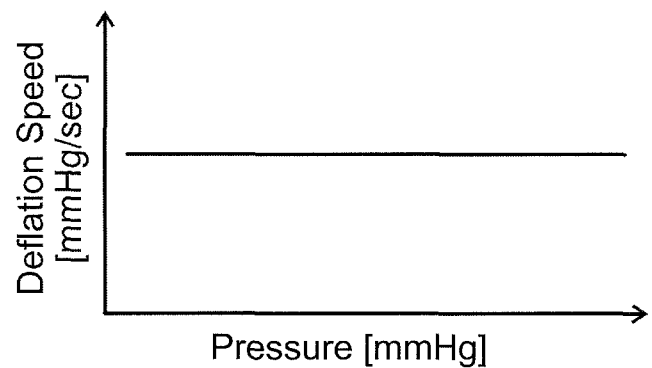
FIG. 29A is a diagram showing the relationship between the pressure of the fluid bag and deflation speed in a sphygmomanometer that deflates the fluid bag at a constant speed.
Figure 29B:
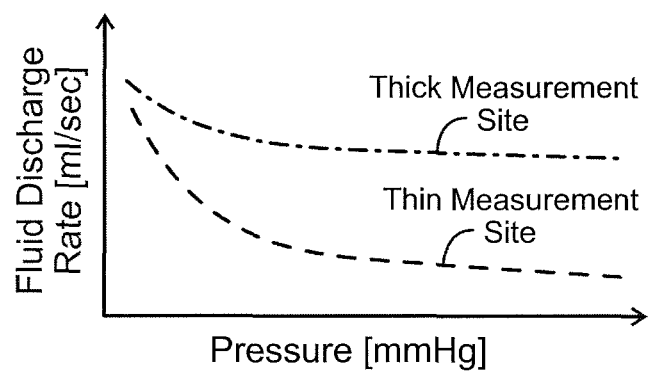
FIG. 29B is a diagram showing the relationship between the pressure of the fluid bag and the discharge rate of fluid in a sphygmomanometer that deflates the fluid bag at a constant speed.
Figure 29C:
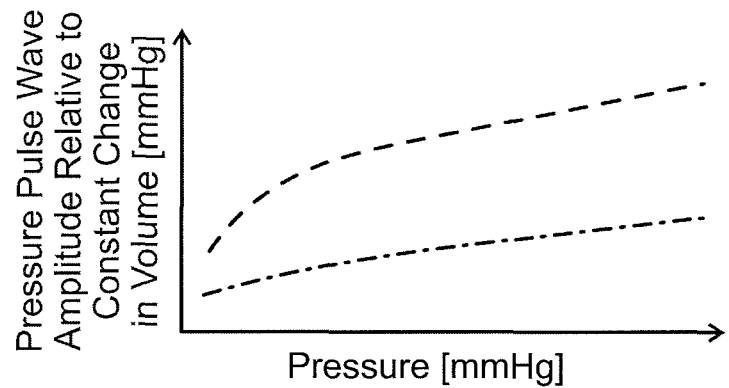
FIG. 29C is a diagram showing the relationship between the pressure of the fluid bag and the pressure pulse wave amplitude value relative to a constant change in volume in the sphygmomanometer that deflates the fluid bag at a constant speed.

(A) in FIG. 11 shows the change in pressure of the fluid bag 13 over time, and the change in intra-arterial pressure. The dotted line A in (A) of FIG. 11 shows a conventional change in pressure of the fluid bag 13 in the case where control is performed so as to deflate the pressure of the fluid bag at a uniform speed. In contrast, in the sphygmomanometer 1, the change in pressure of the fluid bag 13 in the case of deflating the fluid bag by performing control such that the drive voltage E is constant, that is, such that the gap of the regularity 22 is constant is shown by the solid line B. As a result of the fluid bag being deflated by performing control such that the drive voltage E is constant, that is, such that the gap of the valve 22 is constant, conventionally intra-arterial pressure measured in accordance with the change in pressure (deflation) of the fluid bag 13 as shown to (B) of FIG. 11 is measured as shown in (C) of FIG. 11. Specifically, in (C) of FIG. 11, the line segment obtained by connecting each measured value of intra-arterial pressure shown in (B) of FIG. 11 is shown by the dotted line. In a conventional sphygmomanometer controlled so as to deflate the pressure of the fluid bag at a uniform speed, the detection accuracy of changes in the volume of blood vessels decreases in areas where the pressure of the fluid bag is low as compared with areas where the pressure is high, even at the same intra-arterial pressure, as shown in FIG. 25 and FIG. 26. In contrast, with the sphygmomanometer 1, as shown by comparing (B) and (C) of FIG. 11, it is notably shown that the detection accuracy of changes in the volume of blood vessels in areas where the pressure of the fluid bag 13 is low is greater than the detection accuracy of a conventional sphygmomanometer controlled to deflate the pressure of the fluid bag at a uniform speed. Similarly, it is shown that the detection accuracy of changes in the volume of blood vessels in areas where the pressure is high also improves.

Figure 12:
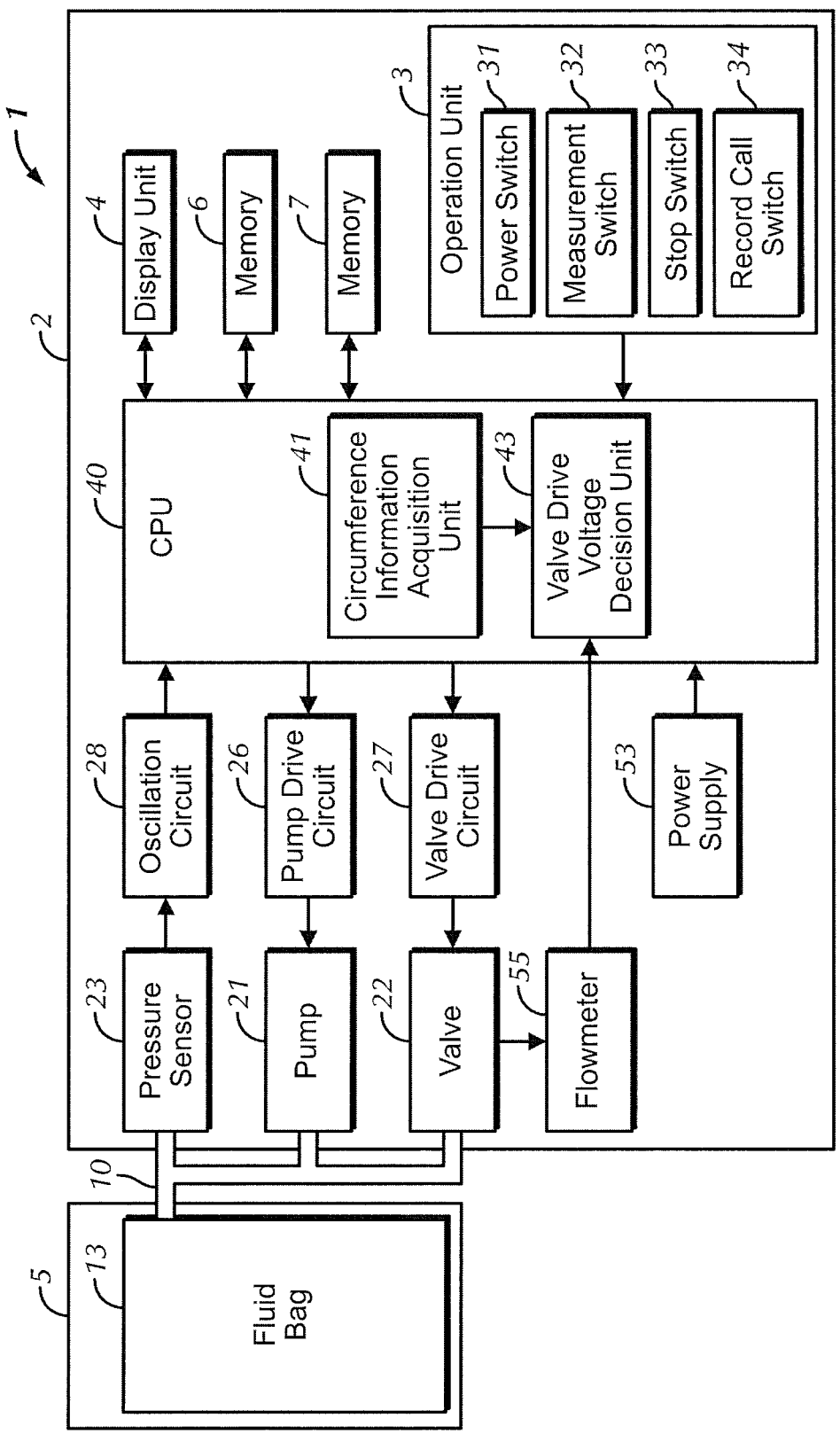
FIG. 12 is a block diagram showing another specific example of the hardware configuration of the sphygmomanometer serving as blood pressure measurement device according to the first embodiment of the present invention.

Note that, in the above example, the CPU 40 performs control so as to hold the drive voltage E at the drive voltage E decided by the valve drive voltage decision unit 43 at the above step S109, that is, to keep the drive voltage E constant, in the deflation process of the above step S111. However, the sphygmomanometer 1 may, in addition to the configuration shown above, further include a flowmeter 55 that measures the discharge rate from the valve 22, such as shown in FIG. 12, and the drive voltage E may be updated by the valve drive voltage decision unit 43 in the deflation process, such that the discharge rate from the valve 22 and the deflation speed are in a proportional relationship. In this case, the CPU 40 performs feedback control, performing control so as to change the drive voltage E to the drive voltage E decided at a specific timing such as a prescribed time interval and hold the resultant drive voltage E. Performing such feedback control enables the flow rate of fluid from the fluid bag 13 and the deflation speed to be approximated closer to a proportional relationship. This enables the pressure pulse wave amplitude relative to a constant change in volume of the blood vessels to be approximated to a constant value, and measurement accuracy to be improved.

Second Embodiment

Figure 13:
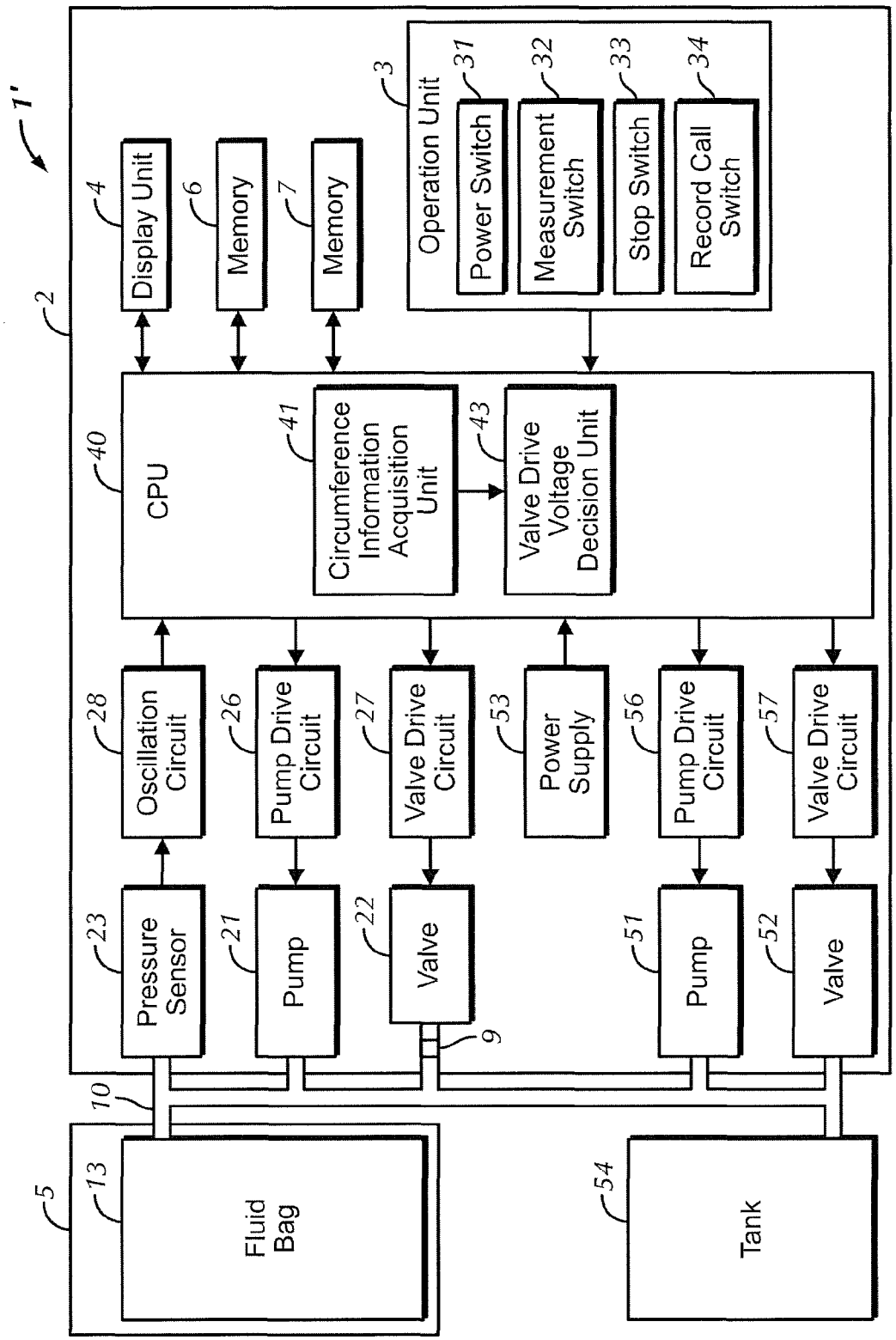
FIG. 13 is a block diagram showing a specific example of the hardware configuration of the sphygmomanometer serving as blood pressure measurement device according to a second embodiment of the present invention.

Referring to FIG. 13, a sphygmomanometer 1' serving as a blood pressure measurement device according to a second embodiment of the present invention is further provided with a tank 54 for storing an incompressible fluid that is connected to the fluid bag 13 by the tube 10, in addition to the hardware configuration of the sphygmomanometer 1 of the first embodiment shown in FIG. 1. The tank 54 is connected to a pump 51 and a valve 52. The pump 51 and the valve 52 are respectively connected to a pump drive circuit 56 and a valve drive circuit 57, and, further, the pump drive circuit 56 and the valve drive circuit 57 are each connected to the CPU 40. The CPU 40, by executing a prescribed program stored in the memory 6 based on an operation signal input from the operation unit 3, decides a voltage for driving the pump 51 and the valve 52, and outputs a control signal according to the decided voltage to the pump drive circuit 56 and the valve drive circuit 57. The incompressible fluid stored in the tank 54 flows into the fluid bag 13 via the tube 10, by driving the pump 51. The incompressible fluid in the fluid bag 13 is discharged by driving the valve 52.

A filter 9 is provided in the portion connecting the fluid bag 13 and the valve 22. In order to prevent the incompressible fluid from leaking out from the valve 22 for injecting fluid into the fluid bag 13 and discharging fluid from the fluid bag 13 when the incompressible fluid in the tank 54 moves to the fluid bag 13, according to one or more embodiments of the present invention, the material of the filter 9 is a material that transmits the fluid but does not transmit the incompressible fluid.

Figure 14:
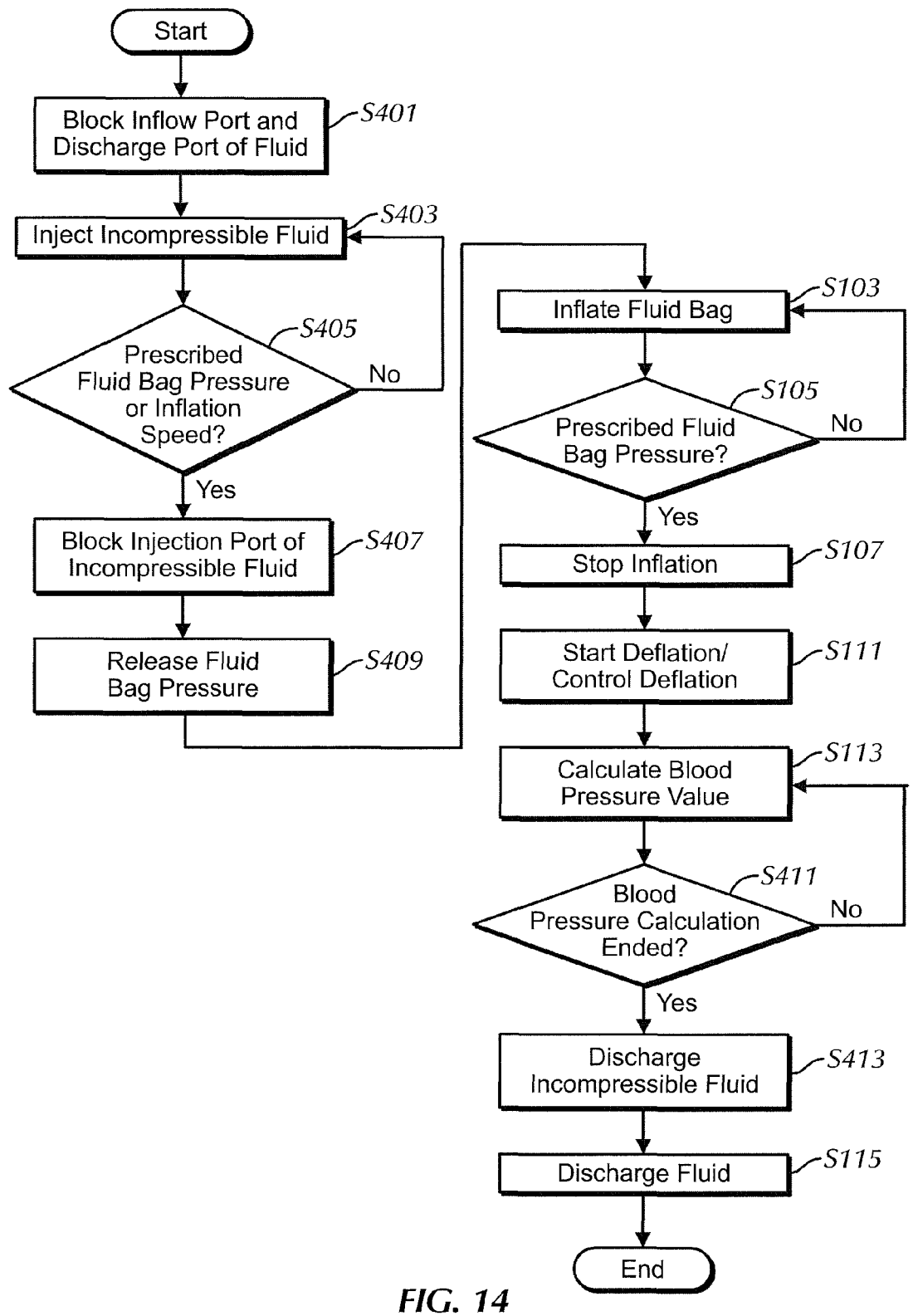
FIG. 14 is a flowchart showing a specific example of processing executed at the timing at which the measurement switch is operated in the sphygmomanometer according to the second embodiment of the present invention.

FIG. 14 is a flowchart showing a specific example of processing executed at the timing at which the measurement switch 32 is operated in the sphygmomanometer 1'. The processing shown in the flowchart of FIG. 14 is realized by the CPU 40 executing a prescribed program stored in the memory 6.

Referring to FIG. 14, in the sphygmomanometer 1', the CPU 40, at step S401, outputs a control signal to the valve drive circuit 27 to close the valve 22, blocking the inflow port and discharge port of fluid to the fluid bag 13. Thereafter, a control signal is output to the pump drive circuit 56 at step S403 to drive the pump 51, and the incompressible fluid in the tank 54 is allowed to flow to the fluid bag 13 until the fluid bag 13 reaches a prescribed inflation pressure defined in advance or reaches a prescribed inflation speed. In other words, the incompressible fluid is moved from the tank 54 to the fluid bag 13. Once the internal pressure of the fluid bag 13 reaches a prescribed pressure, or once the inflation speed of the fluid bag 13 reaches a prescribed inflation speed (YES at step S405), the CPU 40, at step S407, output a control signal to the valve drive circuit 57 to close the valve 52, blocking the inflow port of the incompressible fluid to the fluid bag 13. After blocking the inflow port, the CPU 40, at step S409, then outputs a control signal to the valve drive circuit 27 to open the valve 22, releasing the pressure in the fluid bag 13. A prescribed amount of the incompressible fluid is thereby injected into the fluid bag 13, and, further, the internal pressure equalizes with atmospheric pressure.

Thereafter, the processing of steps S103 to S107, which is similar to the processing according to the first embodiment, is executed, the fluid bag 13 is inflated until the fluid bag 13 reaches a prescribed pressure defined in advance, and the inflation of the fluid bag 13 is stopped in this state. Thereafter, a blood pressure value is calculated at step S113 while the fluid bag 13 is deflated at step S111.

In the sphygmomanometer 1', once calculation of a blood pressure value has ended (YES at step S411), the CPU 40, at step S413, outputs a control signal to the valve drive circuit 57 to open the valve 52, discharging the incompressible fluid in the fluid bag 13. Thereafter, the valve 22 is opened in accordance with a control signal from the CPU 40, and the fluid in the fluid bag 13 is discharged.

Figure 24:
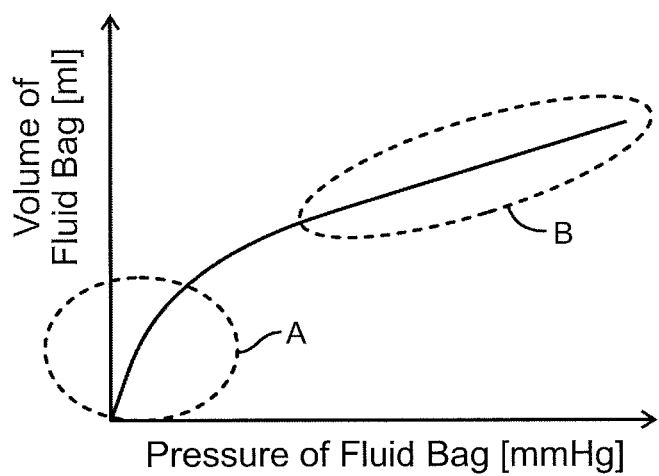
FIG. 24 is a diagram illustrating the characteristics of the fluid bag.

The sphygmomanometer 1' is characterized by injecting a prescribed amount of an incompressible fluid into the fluid bag 13 prior to inflation of the fluid bag 13 in the above step S103, to increase the volume of the fluid bag 13 and reduce the volume of the fluid that is injected. As previously described using FIG. 24, a change in volume of the fluid bag 13 in the area where the internal pressure of the fluid bag 13 is low, shown by portion A in FIG. 24, is thereby suppressed, as compared with the method in which the fluid bag 13 is filled with only the fluid from an initial state. Thus, with the sphygmomanometer 1', the detection accuracy of changes in the volume of blood vessels can be improved.

Figure 15A:
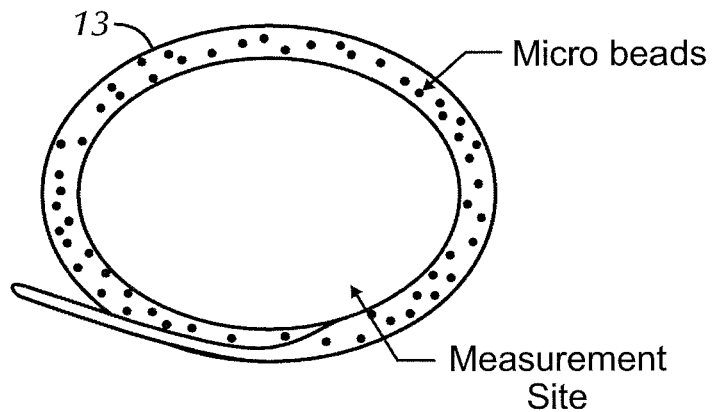
FIG. 15A is a diagram showing another specific example of the configuration of the sphygmomanometer according to the second embodiment of the present invention.
Figure 15B:
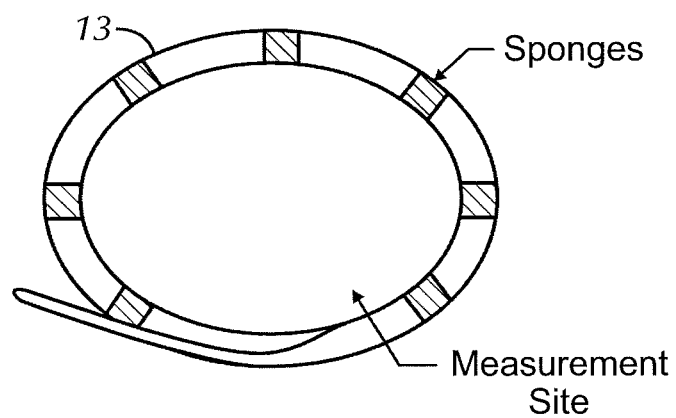
FIG. 15B is a diagram showing another specific example of the configuration of the sphygmomanometer according to the second embodiment of the present invention.
Figure 15C:
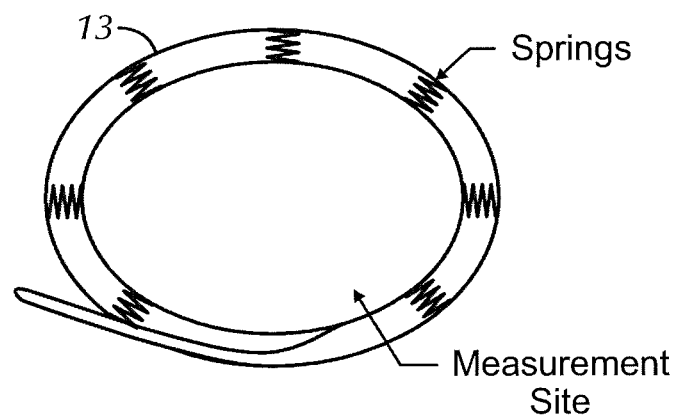
FIG. 15C is a diagram showing another specific example of the configuration of the sphygmomanometer according to the second embodiment of the present invention.

Note that although an incompressible fluid is injected into the fluid bag 13 in the above example as a mechanism for suppressing a change in volume of the fluid bag 13 in a low pressure area, a filling member may be deployed in the fluid bag 13 in advance, as another specific example of the above mechanism. For example, a method in which a gel material such as micro beads is poured into the fluid bag 13 in advance as a filling member may also be adopted, as shown in FIG. 15A. Also, for example, an elastic material such as sponges or springs may be deployed in the fluid bag 13 in advance as a filling member, as shown in FIG. 15B and FIG. 15C. The volume of the fluid bag 13 can be increased prior to inflation by deploying these filling members in the fluid bag 13 in advance. Note that the filling member is not limited to the above-mentioned gel material or elastic material, and may be other materials. Also, the filling member may be a combination of a plurality of these materials.

Further, the control at the time of deflation according to the first embodiment, and the configuration according to the second embodiment may be combined. In other words, in the processing of the sphygmomanometer 1', the processing of the above step S109 may be performed after stopping the inflation of the fluid bag 13 at the above step S107, and the fluid bag 13 may be deflated while performing control such that the gap of the valve 22 is constant. This enables the flow rate and deflation speed of fluid from the fluid bag 13 to be approximated closer to a proportional relationship. This enables the detection accuracy of changes in the volume of blood vessels to thereby be approximated to a constant value, and measurement accuracy to be improved.

Third Embodiment

In the above first embodiment and second embodiment, the discharge rate from the valve 22 and the deflation speed of the fluid bag 13 are placed in a proportional relationship by holding the gap of the valve 22 constant through performing control so as to hold the drive voltage E constant. However, an exhaust valve is readily affected by factors such as production tolerance of the valve and environmental conditions.

Specifically, examples of common exhaust valves include a type (A type) that opens and closes the valve by a thrust force resulting from a magnetic force produced when electric current is fed to a coil, for example, and a type (B type) whose exhaust port is constituted by only rubber having a slit (open/close aperture) and gradually exhausts the fluid. The A type further includes a type (A-1 type) provided with a mechanism for controlling the closed gap of the valve by utilizing gravity to reciprocatively move (raise or lower) a coil in the thrust direction or the gravity direction, and a type (A-2 type) in which control is only possible to fully open or fully close the valve. Exhaust valves other than the above A-1 type are not able to perform fine open/close control, and, further, the A-2 type exhaust valve is only capable of performing control to fully open or fully close the valve. Also, with the above B-type exhaust valve, the slit becomes smaller when pressure increases and becomes larger when pressure decreases, and the gap of the valve is dependent on the elasticity of the rubber, rather than being arbitrarily controlled. According to one or more embodiments of the present invention, the A-1 type with which the exhaust rate can be controlled is used suitably as the valve 22.

Figure 16:
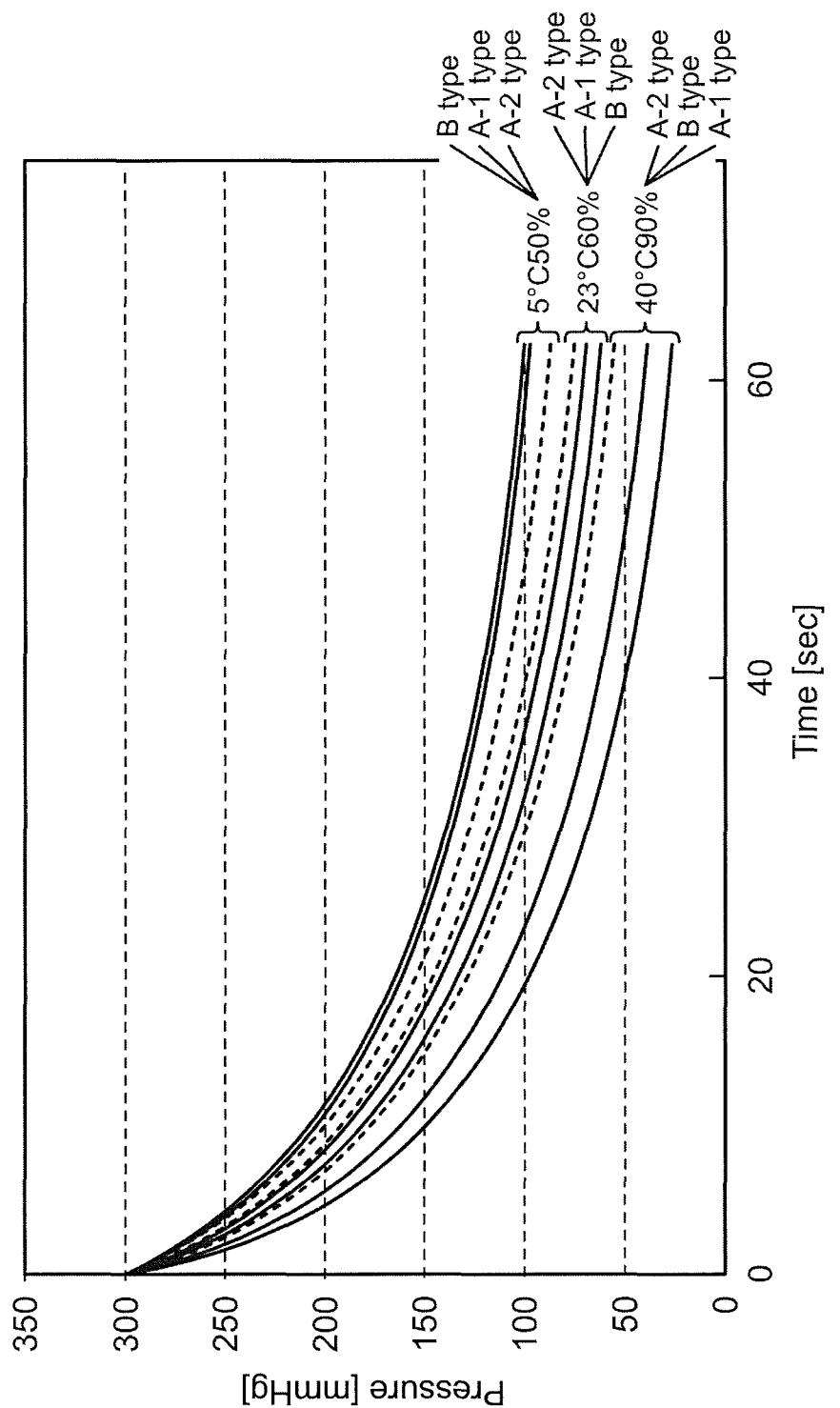
FIG. 16 is a diagram representing the difference in deflation speeds due to the type of exhaust valves for different environmental conditions.

An elastic body such as packing is commonly used in any type of exhaust valve not only in the above A-1 type exhaust valve. Thus, because exhaust characteristics change due to variability in the hardness of the elastic body due to production tolerance, and environmental conditions such as temperature change, the valve 22 is affected thereby. In view of this, the inventors measured deflation speed using three of the above A-1 type exhaust valves manufactured in respectively different production lots, under the same environmental conditions (temperature, humidity). Further, deflation speed was measured under varying environmental conditions (temperature, humidity). As a result of this measurement, it was confirmed that exhaust speed differs due to production tolerance and environmental conditions, even in the case where the same drive voltage was applied, as shown in FIG. 16.

Figure 17:
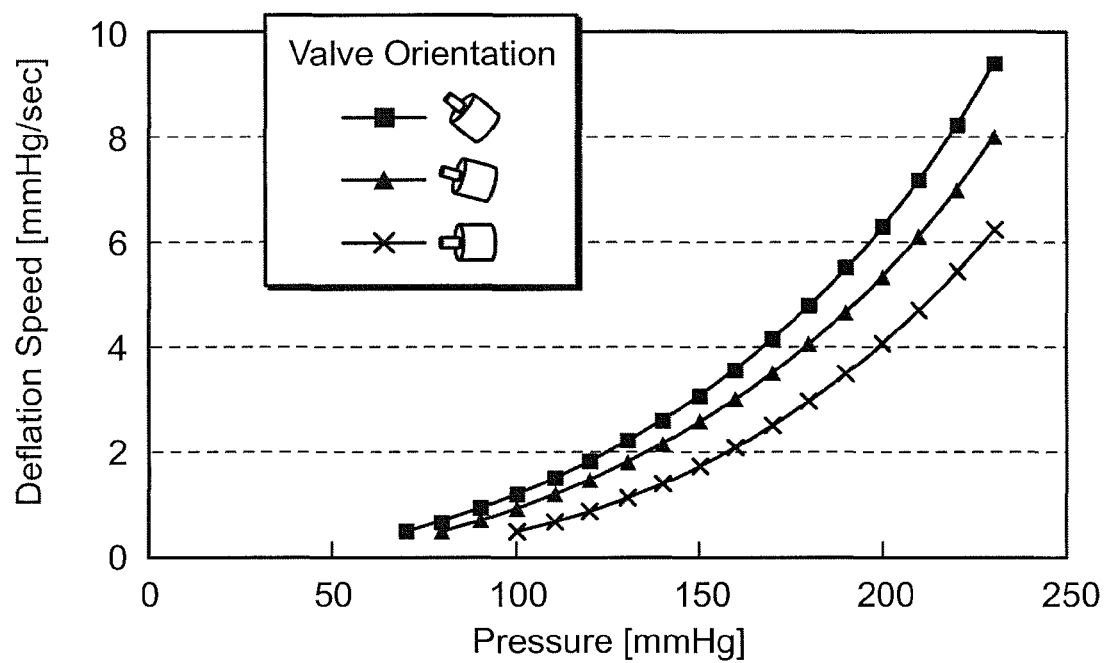
FIG. 17 is a diagram representing the difference in deflation speeds due to the installation orientation of an exhaust valve.

Further, because the gap of the valve is controlled by utilizing gravity to reciprocatively move the coil, the above type A-1 exhaust valve is also affected by the relationship between power in the thrust direction and power in the gravity direction acting on the coil. That is, particularly in the case of using the above type A-1 exhaust valve as the valve 22, the valve is affected by its orientation relative to the gravity direction, that is, the inclination of the sphygmomanometer itself (how the sphygmomanometer is placed). The inventors measured deflation speed for the type A-1 exhaust valve while varying the inclination. As a result of this measurement, it was confirmed that exhaust speed differs due to inclination, even for the same internal pressure of the fluid bag 13, as shown in FIG. 17.

Even if the valve 22 is driven while holding the drive voltage E decided at the above step S109 in the sphygmomanometer 1 or the sphygmomanometer 1', the deflation speed of the fluid bag 13 may not achieve the envisaged deflation speed, due to a change in environmental conditions, production tolerance or placement of the sphygmomanometer, as mentioned above. That is, in comparison to an ideal change in internal pressure of the fluid bag 13 that does not take into consideration the influence of a change in environmental conditions or the like, such as shown by curve (3) in (A) of FIG. 18, a change in internal pressure that differs from an ideal change in internal pressure may result in the case where these influences are felt, as shown by curve (1) and curve (2).

Figure 18:
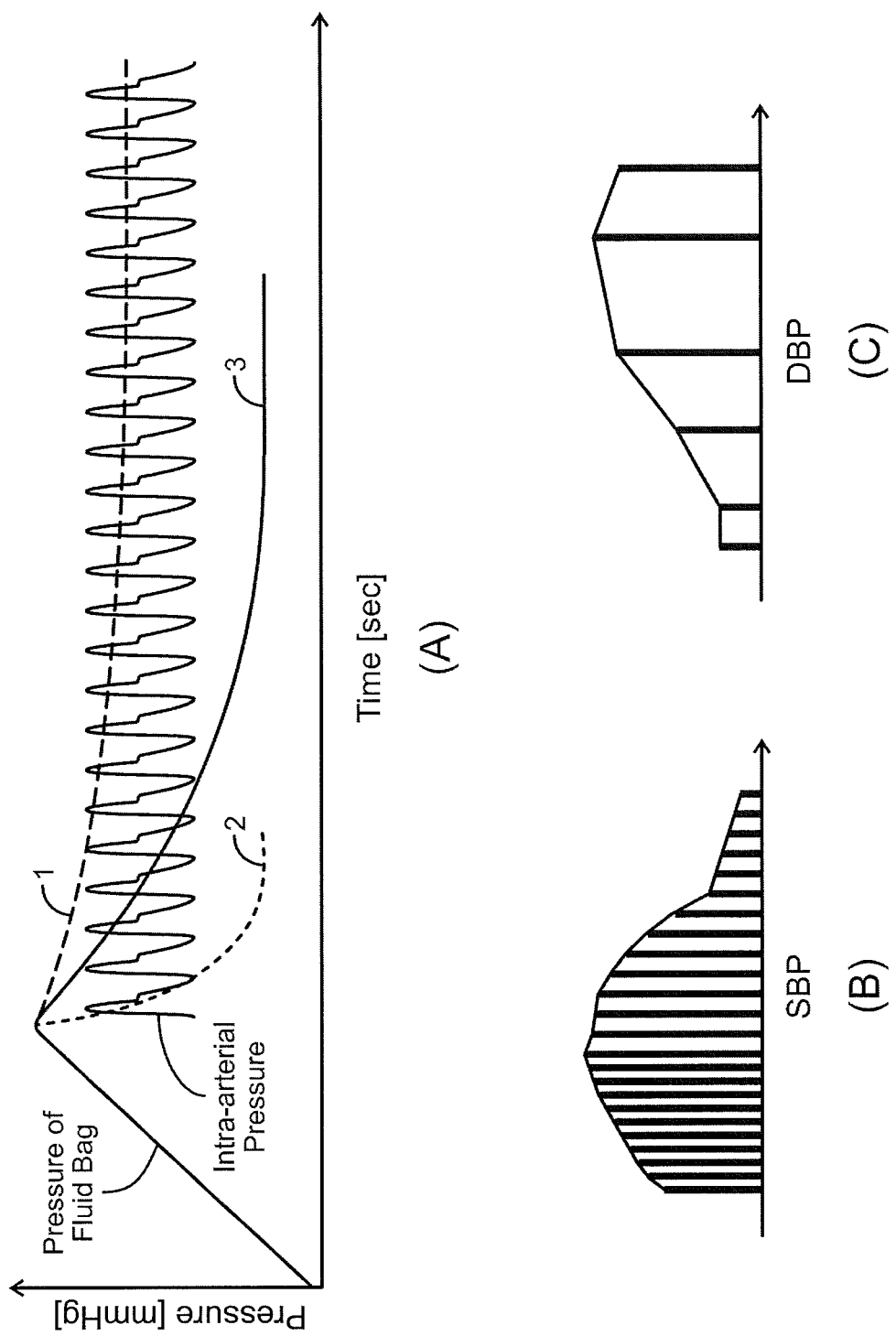
FIG. 18 is a diagram for illustrating the relationship between pressure of the fluid bag and detected pulse wave amplitude.

In the case where the deflation speed is lower than the ideal change in pressure, particularly, on the low pressure side, that is, in the case where the change in internal pressure of the fluid bag 13 is curve (1), the intra-arterial pressure is measured in accordance with the change in pressure (deflation) of the fluid bag 13, as shown in (B) of FIG. 18. In this case, the diastolic blood pressure is not calculated. Otherwise, it takes a long time before the diastolic blood pressure can be calculated, increasing the burden on the person being measured.

In the case where the deflation speed is higher than the ideal change in pressure, particularly, on the high pressure side, that is, in the case where the change in internal pressure of the fluid bag 13 is curve (2), the intra-arterial pressure is measured in accordance with the change in pressure (deflation) of the fluid bag 13 as shown in (C) of FIG. 18. In this case, the systolic blood pressure is not calculated. Otherwise, the calculation accuracy of the blood pressure value decreases.

In view of this, with a sphygmomanometer 1" according to the third embodiment, the drive voltage E of the valve 22 is adjusted such that the change in pressure of the fluid bag 13 approximates curve (3), utilizing the following principle. That is, referring to FIG. 19 and FIG. 20, in the deflation process after inflating the fluid bag 13 to a pressure Pmax obtained by adding a pressure a defined in advance to the systolic blood pressure value P1 predicted from the change in internal pressure of the fluid bag 13 in the inflation process, the deflation speed of the fluid bag 13 at the point in time that P2 at which the internal pressure of the fluid bag 13 has deflated by a prescribed pressure from Pmax is reached is set as a target deflation speed defined in advance, such that the internal pressure falls within a range sandwiched between a dashed line A and a dashed line B. Note that in subsequent description, the point at which the internal pressure of the fluid bag 13 reaches the predicted systolic blood pressure value P1 in the inflation process is called the "SBP predicted point", the point at which the internal pressure of the fluid bag 13 is inflated to Pmax is called the "maximum inflation point", the point at which the internal pressure of the fluid bag 13 is deflated from Pmax to P2 is called the "adjustment point", and the point at which the internal pressure of the fluid bag 13 reaches the actual systolic blood pressure value P1' in the deflation process is called the "SBP actual measurement point", as shown in FIG. 20.

Figure 20:
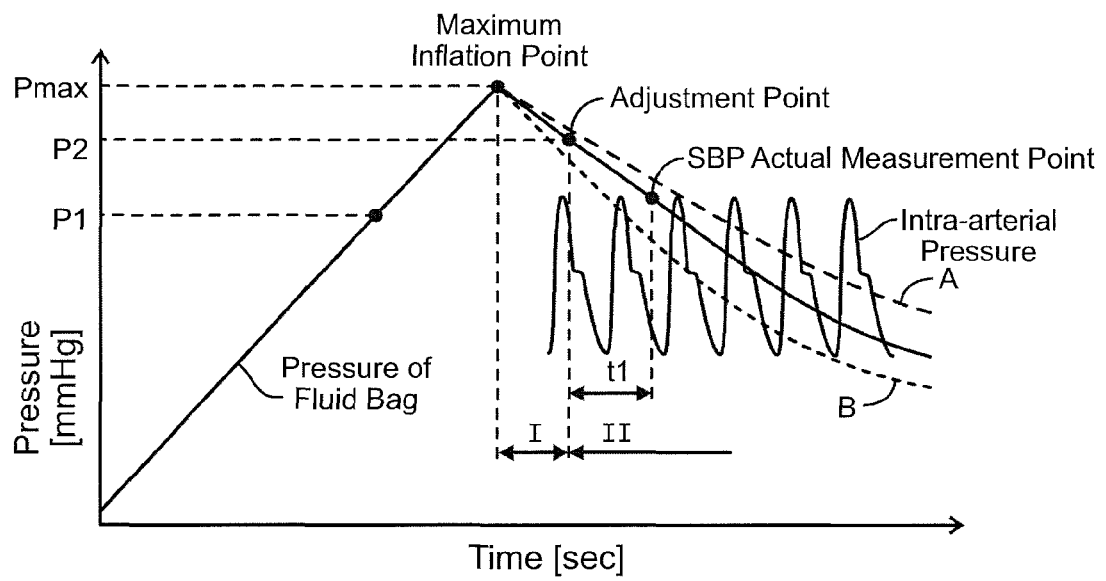
FIG. 20 is a diagram for illustrating a principle for adjusting the drive voltage of an exhaust valve in the sphygmomanometer according to the third embodiment of the present invention.

The dashed line A and the dashed line B shown in FIG. 20 are the upper limit and lower limit of the range of changes in pressure, with there being about 5 mmHg/sec to 20 mmHg/sec between the systolic blood pressure and the diastolic blood pressure during subsequent deflation. In other words, with the range of changes in pressure represented by these dashed lines, at least five pulse beats are measured between the systolic blood pressure and the diastolic blood pressure during subsequent deflation. This is because at least five pulse beats between the systolic blood pressure and the diastolic blood pressure during deflation are required in order to secure measurement accuracy.

Also, referring to FIG. 20, an example is given in which a time t1 from the adjustment point to the SBP actual measurement point is equivalent to at least one pulse beat in time, or about 2 seconds, for example. That is, the adjustment point is a point at least one pulse beat in time before the SBP actual measurement point. This is because in order to calculate the systolic blood pressure value from a measured value, not only the measured value at the SBP actual measurement point but also a measured value at least one pulse beat therebefore or thereafter is required. Further, for a similar reason, the maximum inflation point is also a point at least one pulse beat before the SBP actual measurement point, and the amount of inflation a that is added to the pressure P1 is set based on the time of at least one pulse beat.

Based on this principle, with the sphygmomanometer 1", the drive voltage E of the valve 22 is adjusted such that the deflation speed of the fluid bag 13 between the maximum inflation point and the adjustment point falls within the range of target deflation speeds, and thereafter, the adjusted drive voltage E is held at least until after the calculation of a blood pressure value is completed. From this, the period from the maximum inflation point to the adjustment point represented by a period I in FIG. 19 and FIG. 20 can be viewed as an "(drive voltage E) adjustment period", and the period from then until the calculation of a blood pressure value is completed represented by a period II can be viewed as a "(drive voltage E) fixed period."

It is possible to preset the adjustment point (or adjustment period) and the target deflation speeds, based on the statistical results of a large amount of measurement data, for example. In the sphygmomanometer 1" utilizing the above principle, the adjustment point is preset and stored. As for the adjustment point, a point deflated 20 Hg from the maximum inflation point, that is, Pmax obtained by adding the pressure a to the predicted systolic blood pressure value point P1, can be set, for example. As for the target deflation speed, 15 mmHg/sec can be set, for example. The following specific example is described assuming that these values are set.

Figure 21:
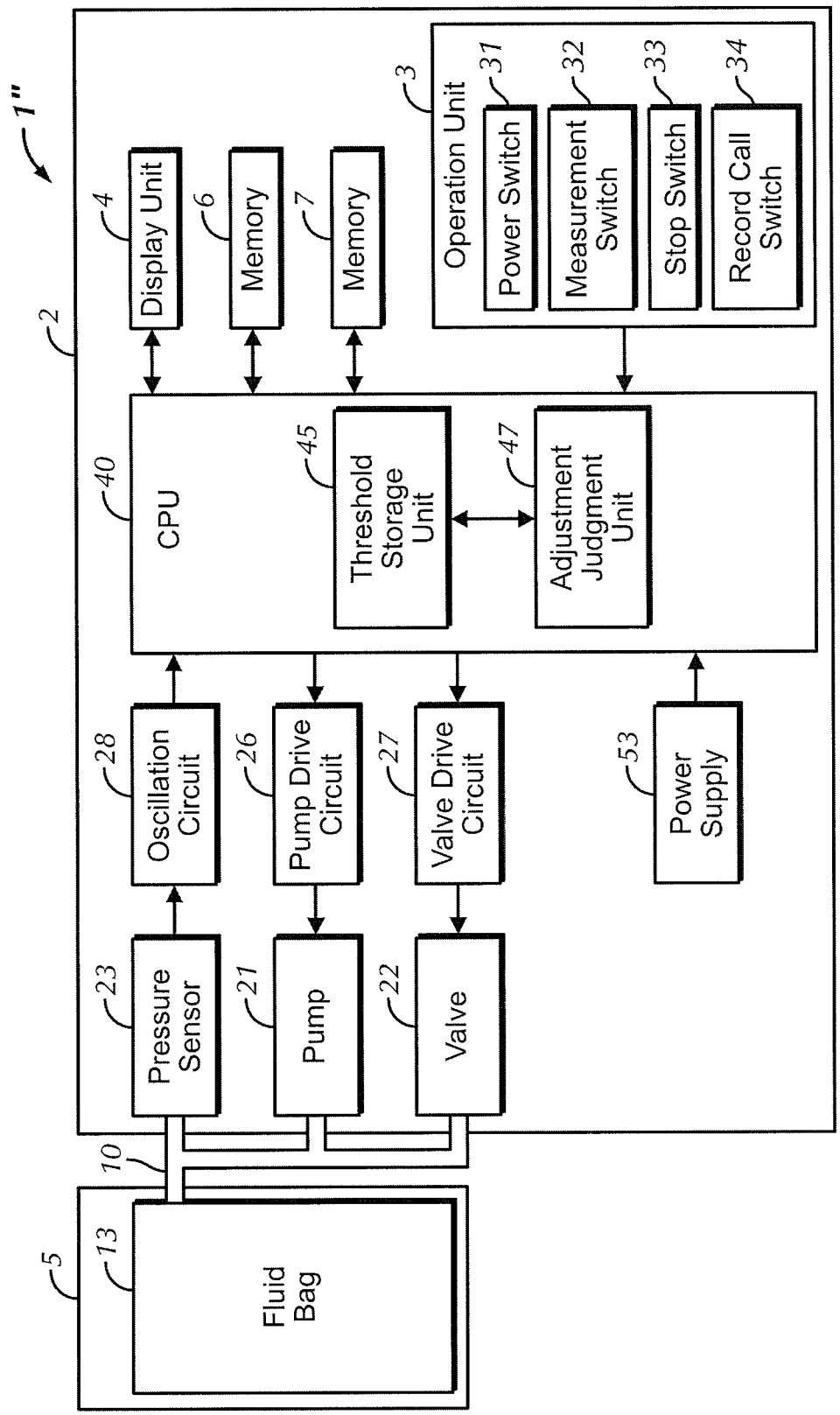
FIG. 21 is a block diagram showing a specific example of a hardware configuration of the sphygmomanometer according to the third embodiment of the present invention.

Referring to FIG. 21, with the sphygmomanometer 1", in order to measure blood pressure using the above principle, the CPU 40 includes a threshold storage unit 45 and an adjustment judgment unit 47 instead of the circumference information acquisition unit 41 and the valve drive voltage decision unit 43, out the hardware configuration of the sphygmomanometer 1 of the first embodiment shown in FIG. 1. These are formed in the CPU 40 as a result of the CPU 40 executing a prescribed program stored in the memory 6 based on an operation signal input from the operation unit 3. The threshold storage unit 45 stores a target deflation speed. The stored target deflation speed may be a constant range. The adjustment judgment unit 47 decides the drive voltage E of the valve 22 based on the change in internal pressure of the fluid bag 13, and adjusts the drive voltage E by comparing the deflation speed of the fluid bag 13 with the stored target deflation speed.

Figure 22:
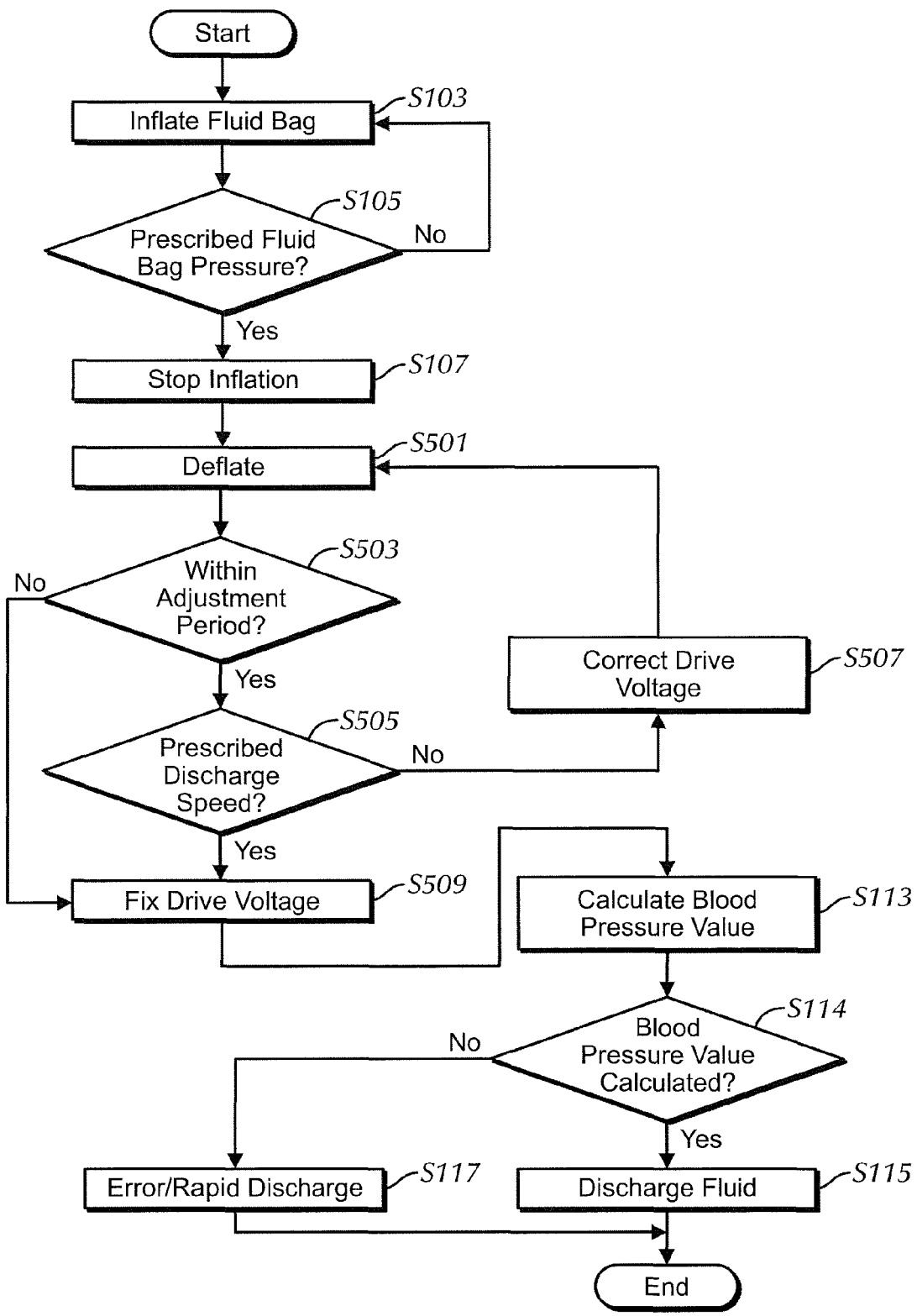
FIG. 22 is a flowchart showing a specific example of processing executed with the sphygmomanometer according to the third embodiment of the present invention.

FIG. 22 is a flowchart showing a first specific example of processing executed at the timing at which the measurement switch 32 is operated in the sphygmomanometer 1." The processing shown in the flowchart of FIG. 22 is realized as a result of the CPU 40 executing a prescribed program stored in the memory 6. In FIG. 22, processing that is given the same step number as the flowchart of FIG. 2 is similar to processing in the sphygmomanometer 1.

Referring to FIG. 22, the CPU 40 monitors input of operation signals from the operation unit 3, and, when operation of the measurement switch 32 is detected, outputs a control signal to the pump drive circuit 26 at step S103 and S105 without performing the acquisition of circumference information of step S101 in the sphygmomanometer 1, and inflates the fluid bag 13 until the fluid bag 13 reaches a prescribed pressure defined in advance. When the prescribed pressure is reached (YES at step S105), the CPU 40, at step S107, outputs a control signal to the pump drive circuit 26, and stops inflation of the fluid bag 13. This point is equivalent to the maximum inflation point.

Thereafter, steps S501 to S509 are processed instead of the processing for deciding the drive voltage E of step S109. That is, after stopping inflation of the fluid bag 13 at step S107, a control signal is output to the pump drive circuit 26 at step S501, and deflation is started. In the deflation process, in the case where it is within the adjustment period, that is, in the case where the difference between the internal pressure of the fluid bag 13 and the internal pressure Pmax of the maximum inflation point is less than 20 mmHg (YES at S503), the CPU 40 compares the deflation speed of the internal pressure of the fluid bag 13 with 15 mmHg/sec, which is the target deflation speed stored in the threshold storage unit 45, in the adjustment judgment unit 47, and if it does not match, or if it is not within a prescribed range from 15 mmHg/sec (NO at S503), corrects the current drive voltage of the present valve 22 at step S507 by adding a correction amount ΔV defined in advance. Alternatively, the following arithmetic operation, for example, may be performed to calculate the correction amount ΔV, and the drive voltage E may be corrected:

$$\Delta V = A(Vt-V)+B,$$

where A is a correction coefficient (gain), B is a correction coefficient (offset), Vt is the target deflation speed, and V is the deflation speed of the fluid bag 13.

Correction of the drive voltage E at these steps S505 and S507 is repeated within the adjustment period until the deflation speed of the internal pressure of the fluid bag 13 matches or falls within a prescribed range of the target deflation speed 15 mmHg/sec. In the case where the deflation speed of the internal pressure of the fluid bag 13 matches or falls within a prescribed range of the target deflation speed 15 mmHg/sec (YES at S505), or in the case where the adjustment period ends, that is, where the internal pressure of the fluid bag 13 is deflated by more than 20 mmHg from the internal pressure Pmax of the highest inflation point (NO at S503), the CPU 40 decides the drive voltage E set at that point in time as the subsequent drive voltage E of the valve 22 in the adjustment judgment unit 47, holds the drive voltage E, outputs a control signal to the valve drive circuit 27 so as to drive the valve 22, and continues deflation of the fluid bag 13.

Subsequently, a blood pressure value is calculated from the measured value with the drive voltage E fixed at step S505, similarly to steps S113 to S117 of FIG. 2, and the series of processes is completed.

As a result of the above processing being performed by the sphygmomanometer 1", the drive voltage E of the valve 22 is adjusted during the period from the maximum inflation point to the adjustment point, the influence of production tolerance, change in environmental conditions, and placement (state of inclination) on the valve 22 can be eliminated, and the change in pressure of the fluid bag 13 can be approximated to curve (3) of (A) of FIG. 18. Even in the case where the valve 22 is affected by production tolerance, change in environmental conditions or placement (state of inclination), the detection accuracy of changes in the volume of blood vessels can thereby be approximated to a constant value, and measurement accuracy can be improved.

Also, processing for acquiring circumference information, and the processing for deciding the drive voltage E according to the circumference that was required with the sphygmomanometer 1 and the like is no longer necessary as a result of performing such control. The overall measurement time can thereby be shortened, and the burden on the subject can be lightened.

Note that the drive voltage E of the valve 22 is assumed to be fixed in the voltage after adjustment during a fixed period after the adjustment point in the above example, although in the case where the difference (blood pressure range) between the systolic blood pressure and the diastolic blood pressure of the person being measured is large, the internal pressure of the fluid bag 13 may stay within blood pressure range for a long time, even after the measurement required for calculating the blood pressure value has ended. An example of the measurement required for calculating the blood pressure value includes a measurement for which about 5 pulse beats are measured between the systolic blood pressure and the diastolic blood pressure during deflation as was previously mentioned. Accordingly, because the measurement site will continue to be compressed by the fluid bag 13 when measurement is continued for longer than this, the burden on the person being measured increases. In view of this, according to one or more embodiments of the present disclosure, the CPU 40 of the sphygmomanometer 1" executes the processing shown in FIG. 23.

Figure 23:
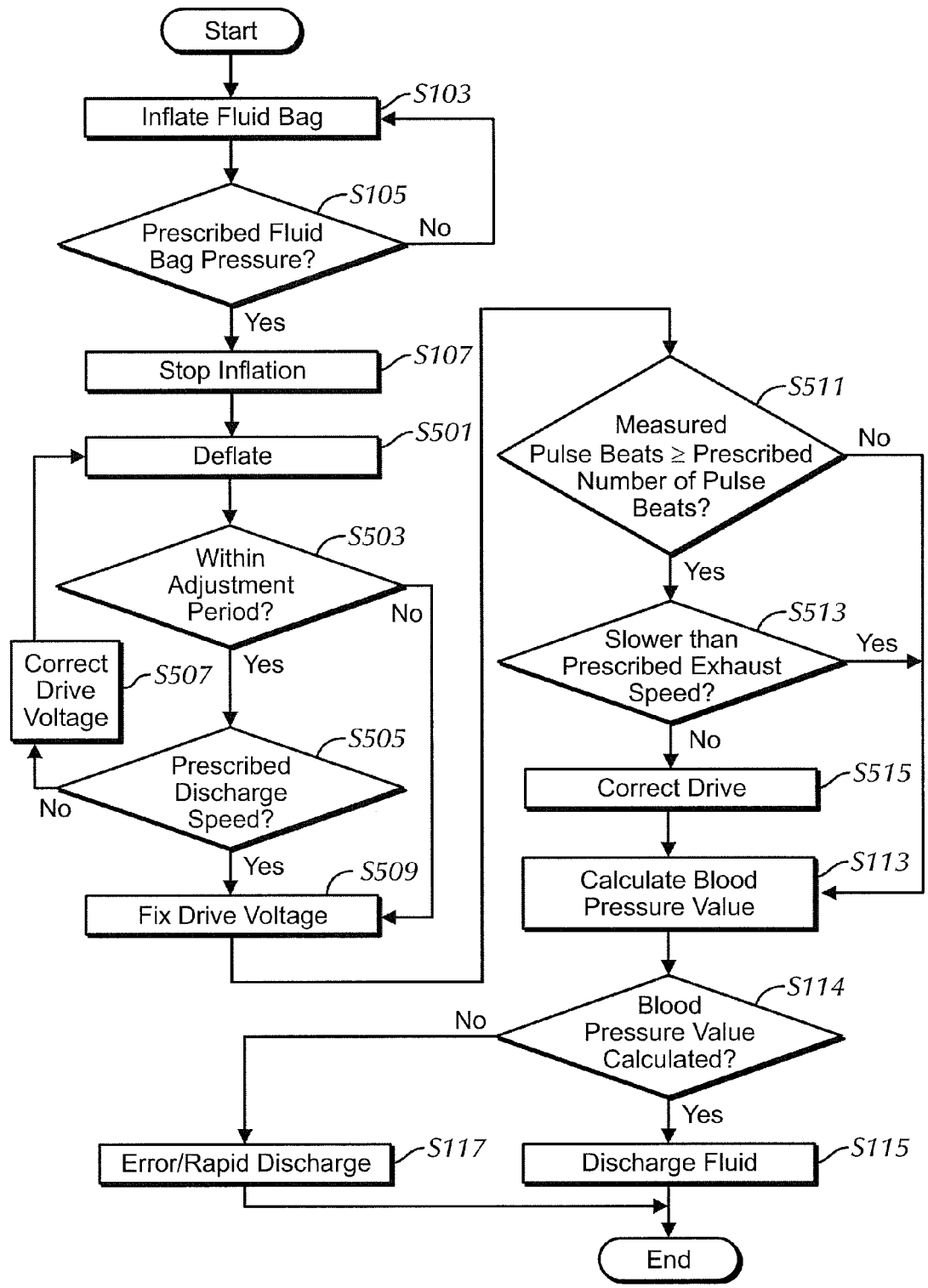
FIG. 23 is a flowchart showing another specific example of the processing executed with the sphygmomanometer according to the third embodiment of the present invention.

That is, referring to FIG. 23, the CPU 40, after performing similar processing as mentioned above until step S509, monitors the number of the pulse beats measured from the change in internal pressure of the fluid bag 13 in subsequent measurement processing in the adjustment judgment unit 47. "5" or the like, for example, is stored in advance in the adjustment judgment unit 47 as the number of pulse beats required for calculating a blood pressure value. When it is detected that the number of the measured pulse beats is equal to or greater than the stored number of required pulse beats (YES at S511), the adjustment judgment unit 47 compares the deflation speed of the internal pressure of the fluid bag 13 with a deflation speed serving as a threshold for judging an appropriate deflation speed stored in advance in the threshold storage unit 45. In the case where the deflation speed of the internal pressure of the fluid bag 13 is lower than the deflation speed serving as a threshold, that is, in the case where the deflation speed is slow (NO at S513), the adjustment judgment unit 47, at step S515, adds a correction amount ΔV' defined in advance, and corrects the current drive voltage of the valve 22. Alternatively, the correction amount ΔV' may be calculated similarly to the correction amount ΔV.

In this way, the burden on a person being measured who has a wide blood pressure range can be reduced by additionally adjusting the drive voltage E of the valve 22 at the stage at which the internal pressure of the fluid bag 13 becomes low.

Figure 19:
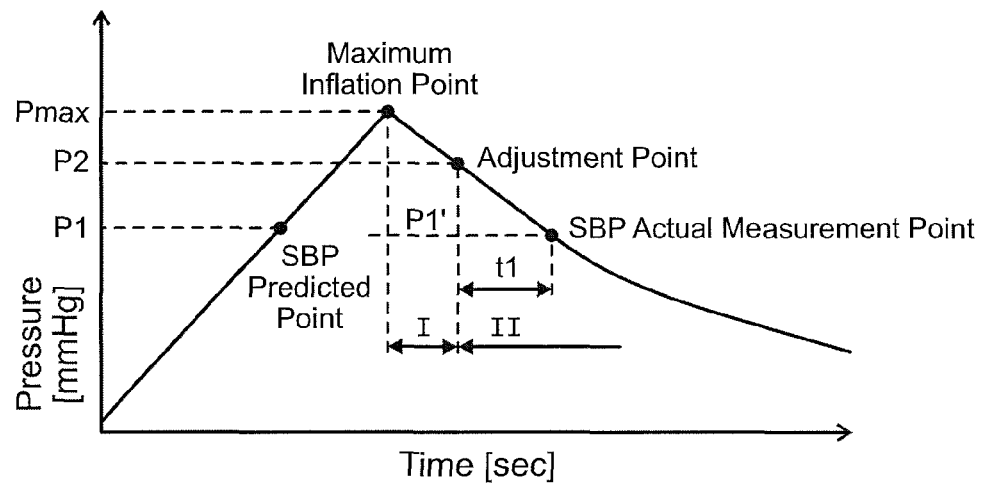
FIG. 19 is a diagram for illustrating a principle for adjusting the drive voltage of an exhaust valve in the sphygmomanometer according to a third embodiment of the present invention.

Note that with the sphygmomanometer 1", the adjustment judgment unit 47 is assumed to compare the deflation speed of the fluid bag 13 with a target deflation speed stored in advance in the threshold storage unit 45, using the principle described using FIG. 19 and FIG. 20. However, this is an example, and another method may be used as long as the drive voltage E of the valve 22 is adjusted such that the internal pressure of the fluid bag 13 is approximated to an envisaged curve shown by curve (3) in (A) of FIG. 18. For example, in the case where a measurement mechanism that measures the consumption current of the valve 22 is provided, a target current value may be stored in advance in the threshold storage unit 45, and the drive voltage E may be adjusted by comparing the consumption current value in the valve 22 with the stored target current value. Alternatively, the adjustment judgment unit 47 may adjust the consumption current instead of the drive voltage E of the valve 22. Alternatively, a configuration may be adopted in which the threshold storage unit 45 stores the correspondence between environmental conditions, placement (state of inclination) and the like and drive voltages E suitable for those conditions in advance, and the adjustment judgment unit 47 reads out and sets the drive voltage E corresponding to the environmental condition, placement (state of inclination) or the like that is detected. Further, in this case, the adjustment judgment unit 47 may receive input of an environmental condition from the operation unit 3, and use the input environmental condition in adjustment.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1, 1', 1" sphygmomanometer
2 main unit
3 operation unit
4 display unit
5 cuff
6, 7 memory
9 filter
10 tube
13 fluid bag
31 power switch
21 pump
22 valve
23 pressure sensor
26 pump drive circuit
27 valve drive circuit
28 oscillation circuit
32 measurement switch
33 stop switch
34 record call switch
40 CPU
41 circumference information acquisition unit
43 valve drive voltage decision unit
45 threshold storage unit
47 adjustment judgment unit
51 pump
52 valve
53 power supply
54 tank
55 flowmeter
56 pump drive circuit
57 valve drive circuit

The invention claimed is:
1. A blood pressure measurement device comprising:
a fluid bag;
an inflation unit that injects fluid into the fluid bag and inflates the fluid bag;
a deflation unit comprising a voltage controlled valve provided in the fluid bag, and that discharges fluid from the fluid bag and deflates the fluid bag,
wherein the voltage controlled valve is an A-1 type exhaust valve;
a sensor that measures a change in internal pressure of the fluid bag;
a blood pressure measurement unit that calculates a blood pressure value, based on the change in internal pressure of the fluid bag obtained by the sensor in a deflation process of discharging fluid from the fluid bag by the deflation unit; and
a central processing unit (CPU) that controls the inflation unit, the deflation unit and the blood pressure measurement unit,
wherein the CPU controls the inflation unit to inflate the fluid bag to reach a predetermined maximum pressure, calculates within a predetermined adjustment period, which is before reaching a point at which a systolic blood pressure is measured, and which is during the deflation process, a drive voltage to be applied to the voltage controlled valve to cause the deflation unit to deflate the fluid bag at a deflation speed that is a predetermined deflation speed given by a predetermined pressure change per unit time, and maintains, during a drive voltage fixed period occurring after the predetermined adjustment period, the drive voltage at a fixed value equal to the calculated drive voltage.

2. The blood pressure measurement device according to claim 1,
wherein the CPU comprises an adjustment judgment unit that adjusts the drive voltage to be applied to the voltage controlled valve based on a consumption current of the voltage controlled valve.

3. The blood pressure measurement device according to claim 1,
wherein the predetermined deflation speed is characterized by a prescribed range, and
wherein the CPU judges whether the deflation speed of the fluid bag is within the prescribed range by comparing a consumption current of the voltage controlled valve with a threshold.

4. The blood pressure measurement device according to claim 1, wherein the predetermined adjustment period is a period from a start of the deflation process until at least one pulse beat prior to a pulse wave initially being superimposed on the internal pressure of the fluid bag in the deflation process.

5. The blood pressure measurement device according to claim 1, wherein the CPU calculates the drive voltage so as to achieve a deflation speed at which at least a prescribed number of pulse beats is included in a time taken for the internal pressure of the fluid bag to change from the systolic blood pressure to a diastolic blood pressure.

6. An electronic sphygmomanometer control method comprising:
inflating a fluid bag to reach a predetermined maximum pressure;
calculating within a predetermined adjustment period, which is before reaching a point at which a systolic blood pressure is measured, and which is during the deflation process, a drive voltage to be applied to a voltage controlled valve provided in the fluid bag,
wherein the voltage controlled valve is an A-1 type exhaust valve;
applying the calculated drive voltage to the voltage controlled valve to cause deflation of the fluid bag at a deflation speed that is a predetermined deflation speed given by a predetermined pressure change per unit time; and maintaining, during a drive voltage fixed period occurring after the predetermined adjustment period, the drive voltage at a fixed value equal to the calculated drive voltage.

7. The electronic sphygmomanometer control method of claim 6, wherein the drive voltage to be applied to the voltage controlled valve is adjusted based on a consumption current of the voltage controlled valve.

8. The electronic sphygmomanometer control method of claim 6,
wherein the predetermined deflation speed is characterized by a prescribed range, and
wherein the method further comprises judging whether the deflation speed of the fluid bag is within the prescribed range by comparing a consumption current of the voltage controlled valve with a threshold.

9. The electronic sphygmomanometer control method of claim 6,
wherein the systolic blood pressure and a diastolic blood pressure are measured based on a change in internal pressure of the fluid bag in a deflation process after the predetermined adjustment period,
wherein the drive voltage fixed period is a period from a start of the deflation process until at least one pulse beat prior to a pulse wave initially being superimposed on the internal pressure of the fluid bag in the deflation process.

10. The electronic sphygmomanometer control method of claim 6,
wherein the systolic blood pressure and a diastolic blood pressure are measured based on a change in internal pressure of the fluid bag in a deflation process after the predetermined adjustment period, and
wherein the drive voltage is calculated so as to achieve a deflation speed at which at least a prescribed number of pulse beats is included in a time taken for the internal pressure of the fluid bag to change from the systolic blood pressure to the diastolic blood pressure.

11. A non-transitory computer readable medium having stored thereon a program that causes a CPU to execute a method of controlling an electronic sphygmomanometer, the method comprising:
inflating a fluid bag to reach a predetermined maximum pressure;
calculating within a predetermined adjustment period, which is before reaching a point at which a systolic blood pressure is measured, and which is during the deflation process, a drive voltage to be applied to a voltage controlled valve provided in the fluid bag, wherein the voltage controlled valve is an A-1 type exhaust valve;
applying the calculated drive voltage to the voltage controlled valve to cause deflation of the fluid bag at a deflation speed that is a predetermined deflation speed given by a predetermined pressure change per unit time; and
maintaining, during a drive voltage fixed period occurring after the predetermined adjustment period, the drive voltage at a fixed value equal to the calculated drive voltage.

12. The method according to claim 11, wherein the drive voltage to be applied to the voltage controlled valve is calculated based on a consumption current of the voltage controlled valve.

13. The method according to claim 11,
wherein the predetermined deflation speed is characterized by a prescribed range, and
wherein the method further comprises judging whether the deflation speed of the fluid bag is within the prescribed range by comparing a consumption current of the voltage controlled valve with a threshold.

14. The method according to claim 11,
wherein the systolic blood pressure and a diastolic blood pressure are measured based on a change in internal pressure of the fluid bag in a deflation process after the predetermined adjustment period,
wherein the drive voltage fixed period is a period from a start of the deflation process until at least one pulse beat prior to a pulse wave initially being superimposed on the internal pressure of the fluid bag in the deflation process.

15. The method according to claim 11,
wherein the systolic blood pressure and a diastolic blood pressure are measured based on a change in internal pressure of the fluid bag in a deflation process after the predetermined adjustment period, and
wherein the drive voltage is calculated so as to achieve a deflation speed at which at least a prescribed number of pulse beats is included in a time taken for the internal pressure of the fluid bag to change from the systolic blood pressure to the diastolic blood pressure.

* * * * *